(12) United States Patent
Kapoor et al.

(10) Patent No.: US 6,989,473 B1
(45) Date of Patent: Jan. 24, 2006

(54) **METHOD OF MAKING MALE STERILE *PETUNIA* PLANTS BY TRANSFORMATION WITH A NUCLEIC ACID ENCODING A ZINC FINGER TRANSCRIPTIONAL FACTOR**

(75) Inventors: Sanjay Kapoor, Ibaraki (JP); Akira Kobayashi, Hokkaido (JP); Hiroshi Takatsuji, Ibaraki (JP)

(73) Assignee: Incorporated Administrative Agency National Agriculture and Bio-Oriented Research Organization, Ibaraki (JP)

( * ) Notice: Subject to any disclaimer, the term of this patent is extended or adjusted under 35 U.S.C. 154(b) by 0 days.

(21) Appl. No.: 10/130,731

(22) PCT Filed: Nov. 19, 1999

(86) PCT No.: PCT/JP99/06467

§ 371 (c)(1),
(2), (4) Date: Aug. 6, 2002

(87) PCT Pub. No.: WO01/37643

PCT Pub. Date: May 31, 2001

(51) Int. Cl.
*C12N 15/82* (2006.01)

(52) U.S. Cl. .................. 800/303; 800/290; 800/285

(58) Field of Classification Search ............... 800/290, 800/285, 286
See application file for complete search history.

(56) References Cited

U.S. PATENT DOCUMENTS 6,559,357 B1 * 5/2003 Fischer et al. ............. 800/290

FOREIGN PATENT DOCUMENTS

| EP | 513884 | * 11/1992 |
| WO | WO 95/25787 | 9/1995 |

OTHER PUBLICATIONS

Kater et al, 1998, Plant Cell 10:171-182.*
Colliver et al, 1997, Plant Mol. Biol. 35:509-522.*
Lazar et al, 1998, Mol. Cell. Biol. 8:1247-1252.*
Hill et al, 1998, Biochem. Biophys. Res. Comm. 244:573-577.*
Kobayashi, Akira et al., "Seven zinc-finger transcription factors are expressed sequentially during the development of anthers in petunia", *The Plant Journal* 13(4), 571-576, 1998.
Williams, M. E. et al., "Male sterility through recombinant DNA technology", *Pollen Biotechnology for Crop Production and Improvement*, Shivanna and Sawhney (Eds.), Cambridge University Press, pp. 237-257, 1997.
Takatsuji, H., "Zinc-finger proteins: the classical zinc finger emerges in contemporary plant science", *Plant Molecular Biology* 39:1073-1078, 1999.

* cited by examiner

*Primary Examiner*—Anne Kubelik
(74) *Attorney, Agent, or Firm*—Jacqueline F. Mahoney; Perkins Coie LLP

(57) ABSTRACT

A method is provided for producing a male sterile plant of the family Solanaceae by utilizing a plant expression cassette including a nucleic acid which is DNA encoding zinc finger transcription factors (ZPT2-5) derived from *Petunia* and a promoter operatively linked to the nucleic acid.

5 Claims, 18 Drawing Sheets

FIG. 1

```
atcaaaacca aaattccttt ttcacaccga agaacagcct tagtatttca agaaaac      57
```

| | | | | | | | | | | | | | | | | |
|---|---|---|---|---|---|---|---|---|---|---|---|---|---|---|---|---|
| atg | gtg | gct | cta | tca | acg | aag | aga | gaa | aga | gaa | gaa | gat | aac | ttt | tac | 105 |
| Met | Val | Ala | Leu | Ser | Thr | Lys | Arg | Glu | Arg | Glu | Glu | Asp | Asn | Phe | Tyr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| agc | ata | aca | acc | atg | gca | aat | tac | ttg | atg | tta | ctc | tcg | cgc | caa | gca | 153 |
| Ser | Ile | Thr | Thr | Met | Ala | Asn | Tyr | Leu | Met | Leu | Leu | Ser | Arg | Gln | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| aat | gaa | cat | ttt | gac | aag | aaa | atg | aac | aac | tca | agt | act | agt | cga | gtt | 201 |
| Asn | Glu | His | Phe | Asp | Lys | Lys | Met | Asn | Asn | Ser | Ser | Thr | Ser | Arg | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| ttc | gag | tgc | aag | act | tgt | aat | cgc | cag | ttt | tca | tct | ttt | caa | gca | cta | 249 |
| Phe | Glu | <u>Cys</u> | <u>Lys</u> | <u>Thr</u> | <u>Cys</u> | <u>Asn</u> | <u>Arg</u> | <u>Gln</u> | <u>Phe</u> | <u>Ser</u> | <u>Ser</u> | <u>Phe</u> | <u>Gln</u> | <u>Ala</u> | <u>Leu</u> | |
| | 50 | | | | | 55 | | | | | 60 | | | | | |

| | | | | | | | | | | | | | | | | |
|---|---|---|---|---|---|---|---|---|---|---|---|---|---|---|---|---|
| ggt | ggc | cat | aga | gca | agt | cac | aag | aag | cca | aga | tta | atg | gga | gaa | ttg | 297 |
| <u>Gly</u> | <u>Gly</u> | <u>His</u> | <u>Arg</u> | <u>Ala</u> | <u>Ser</u> | <u>His</u> | Lys | Lys | Pro | Arg | Leu | Met | Gly | Glu | Leu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cat | aac | ttg | caa | tta | ttt | cat | gaa | ttg | cct | aaa | cgt | aaa | act | cac | gag | 345 |
| His | Asn | Leu | Gln | Leu | Phe | His | Glu | Leu | Pro | Lys | Arg | Lys | Thr | His | Glu | |
| | | | 85 | | | | | 90 | | | | | 95 | | | |

| | | | | | | | | | | | | | | | | |
|---|---|---|---|---|---|---|---|---|---|---|---|---|---|---|---|---|
| tgc | tcc | att | tgt | ggg | ctt | gag | ttc | gcc | att | ggg | caa | gct | tta | gga | gga | 393 |
| <u>Cys</u> | <u>Ser</u> | <u>Ile</u> | <u>Cys</u> | <u>Gly</u> | <u>Leu</u> | <u>Glu</u> | <u>Phe</u> | <u>Ala</u> | <u>Ile</u> | <u>Gly</u> | <u>Gln</u> | <u>Ala</u> | <u>Leu</u> | <u>Gly</u> | <u>Gly</u> | |
| | | | 100 | | | | | 105 | | | | | 110 | | | |

| | | | | | | | | | | | | | | | | |
|---|---|---|---|---|---|---|---|---|---|---|---|---|---|---|---|---|
| cat | atg | aga | agg | cat | aga | gct | gtg | ata | aat | gat | aaa | aat | ctt | caa | gct | 441 |
| <u>His</u> | <u>Met</u> | <u>Arg</u> | <u>Arg</u> | <u>His</u> | Arg | Ala | Val | Ile | Asn | Asp | Lys | Asn | Leu | Gln | Ala | |
| | | 115 | | | | | 120 | | | | | 125 | | | | |

| | | | | | | | | | | | | | | | | |
|---|---|---|---|---|---|---|---|---|---|---|---|---|---|---|---|---|
| cct | gat | gat | caa | cat | gct | cct | gtc | gtc | aaa | aaa | gca | aat | ggt | cgg | aga | 489 |
| Pro | Asp | Asp | Gln | His | Ala | Pro | Val | Val | Lys | Lys | Ala | Asn | Gly | Arg | Arg | |
| | | 130 | | | | | 135 | | | | | 140 | | | | |

FIG. 1 (Continued)

```
att ttg tcc ttg gat ttg aac ttg acg cca ttg gaa aat gac tta gag   537
Ile Leu Ser Leu Asp Leu Asn Leu Thr Pro Leu Glu Asn Asp Leu Glu
145                 150                 155                 160 ttt gat ttg cga aag agt aat act gct cct atg gtc gat tgc ttt tta   585
Phe Asp Leu Arg Lys Ser Asn Thr Ala Pro Met Val Asp Cys Phe Leu
                    165                 170                 175 tga ttgaactttc cgtttcctta ttcttttctc ttcttctttt ggatattgta        638
tttattcatt aattgtagga gggataggaa gtcttatctt gtgtattagt actacatttt 698
gcagattgta gaacgattag tttgtaactt atcatgatac ccgaaataca atactattta 758
tatgattatt atactacac                                              777
```

FIG. 2

```
accggtccgg aattcccggg tcgacccacg cgtccggaaa ctttccttgt tgcactttaa  60
tttatgttct agtgagtata ttagagagtg agaa atg gtg gac aat agc cag aaa 115
                                     Met Val Asp Asn Ser Gln Lys
                                     1                 5 aat gaa cca tca act gtt ata cac tat tgt aga gta tgt aaa agg gga  163
Asn Glu Pro Ser Thr Val Ile His Tyr Cys Arg Val Cys Lys Arg Gly
        10                  15                  20 ttt aat agt gct gga gct ctt ggt ggg cac atg aga tct cat gga gtg  211
Phe Asn Ser Ala Gly Ala Leu Gly Gly His Met Arg Ser His Gly Val
        25                  30                  35 gga gat cat aat aaa aac tat ggt gaa gat att aat gaa caa aga tat  259
Gly Asp His Asn Lys Asn Tyr Gly Glu Asp Ile Asn Glu Gln Arg Tyr
40                  45                  50                  55 atg atc aac aac ttt aga aga gat aaa cca gag ggt caa aag cac tca  307
Met Ile Asn Asn Phe Arg Arg Asp Lys Pro Glu Gly Gln Lys His Ser
                60                  65                  70 tat aat ctt cgt gct aat act aat aga tta tta ggc aat cga gca agt  355
Tyr Asn Leu Arg Ala Asn Thr Asn Arg Leu Leu Gly Asn Arg Ala Ser
        75                  80                  85 gaa gat cgt gac aag aag tcc tcg atg tgg cct ccc aat gat cgt ggg  403
Glu Asp Arg Asp Lys Lys Ser Ser Met Trp Pro Pro Asn Asp Arg Gly
        90                  95                  100 aaa tat gcc cta gac gag act cta acc cta tca tca atg tcg tca cca  451
Lys Tyr Ala Leu Asp Glu Thr Leu Thr Leu Ser Ser Met Ser Ser Pro
        105                 110                 115 gga tca tca gat ctt gaa aga agt act aag cca tat gat gca aaa gaa  499
Gly Ser Ser Asp Leu Glu Arg Ser Thr Lys Pro Tyr Asp Ala Lys Glu
120                 125                 130                 135
```

FIG. 2 (Continued)

```
gtg tat aat gga aat gat aag gac aaa tac gct tca aga gaa gaa gaa    547
Val Tyr Asn Gly Asn Asp Lys Asp Lys Tyr Ala Ser Arg Glu Glu Glu
            140                 145                 150 gaa gat cta gcg aat tgt ttg gtc atg ttg tcg aac aaa tct tat gtt    595
Glu Asp Leu Ala Asn Cys Leu Val Met Leu Ser Asn Lys Ser Tyr Val
            155                 160                 165 ttg tcc gat aac aat gag gca aca tac aag gct gaa gaa gtg gaa aag    643
Leu Ser Asp Asn Asn Glu Ala Thr Tyr Lys Ala Glu Glu Val Glu Lys
            170                 175                 180 ggc atg ttc caa tgt aaa gca tgc aag aaa gtt ttt agc tcc cac caa    691
Gly Met Phe Gln Cys Lys Ala Cys Lys Lys Val Phe Ser Ser His Gln
            185                 190                 195 gct tta ggg gga cat aga gcg agt cat aag aaa gtt aaa ggg tgt tat    739
Ala Leu Gly Gly His Arg Ala Ser His Lys Lys Val Lys Gly Cys Tyr
200                 205                 210                 215 gct gcc aag ata aaa gat gac aac gac ggc aac aac gac aac aac gac    787
Ala Ala Lys Ile Lys Asp Asp Asn Asp Gly Asn Asn Asp Asn Asn Asp
            220                 225                 230 aac aac aat aat gat aat gac atc gat gaa gac tcg atc tct cct agt    835
Asn Asn Asn Asn Asp Asn Asp Ile Asp Glu Asp Ser Ile Ser Pro Ser
            235                 240                 245 gat tta att ttc cat caa gaa tct aac tcg ttt cag tct caa tct cca    883
Asp Leu Ile Phe His Gln Glu Ser Asn Ser Phe Gln Ser Gln Ser Pro
            250                 255                 260 tca tca tcg agc tcg ttt tca agg aag aga tca agg gtt cat caa tgc    931
Ser Ser Ser Ser Ser Phe Ser Arg Lys Arg Ser Arg Val His Gln Cys
            265                 270                 275 tcg att tgt cat cga gtt ttt tca tca gga caa gcc ttg ggt ggg cac    979
Ser Ile Cys His Arg Val Phe Ser Ser Gly Gln Ala Leu Gly Gly His
280                 285                 290                 295
```

FIG. 2 (Continued)

```
aaa agg tgt cac tgg cta tca tca agt ttg cca gag aat act ttt ata   1027
Lys Arg Cys His Trp Leu Ser Ser Ser Leu Pro Glu Asn Thr Phe Ile
            300                 305                 310 cca act ttt caa gaa atc caa tac cac acc caa gaa caa gga tta ttc   1075
Pro Thr Phe Gln Glu Ile Gln Tyr His Thr Gln Glu Gln Gly Leu Phe
            315                 320                 325 aac aag cca atg ttt acc aac ttt gat caa cca tta gat cta aac ttc   1123
Asn Lys Pro Met Phe Thr Asn Phe Asp Gln Pro Leu Asp Leu Asn Phe
            330                 335                 340 cca gca caa cta ggc aat cca gct gaa ttt gag ttg aaa cta cac aat   1171
Pro Ala Gln Leu Gly Asn Pro Ala Glu Phe Glu Leu Lys Leu His Asn
        345                 350                 355 cca ttt gaa cat gaa ggc cca aga agc tat ctc cag cta tgg aca gac   1219
Pro Phe Glu His Glu Gly Pro Arg Ser Tyr Leu Gln Leu Trp Thr Asp
360                 365                 370                 375 caa caa atc aat act aat tta cat caa aat gag aag tgc aaa gat tca   1267
Gln Gln Ile Asn Thr Asn Leu His Gln Asn Glu Lys Cys Lys Asp Ser
            380                 385                 390 acg gag gat ttg aga agg gaa gaa aat tac aag gac aag gaa gca aaa   1315
Thr Glu Asp Leu Arg Arg Glu Glu Asn Tyr Lys Asp Lys Glu Ala Lys
        395                 400                 405 ttg agt aac ctt aaa gat gtg aac ttg gat gga ggc tct tct tgg tta   1363
Leu Ser Asn Leu Lys Asp Val Asn Leu Asp Gly Gly Ser Ser Trp Leu
        410                 415                 420 caa gta ggg att ggt cca acc cca gat ata gta gca act ctg taa      1408
Gln Val Gly Ile Gly Pro Thr Pro Asp Ile Val Ala Thr Leu
        425                 430                 435 ggttagtaac acagtgatcg ttatgtcagc tacaagtata gtaatatata taccaatgtc 1468
ccaacttata cataaactgt ttaacatatt tatactttcg tattattgtt gtatcgaact 1528
ttcactagtt acaatttgtg attcgtccaa tccctaatat agtagcaaca gacctgtaag 1588
attagtatta tgcgattgtt ttgtcattct acaaaataaa atcgtataat at        1640
```

FIG. 3

```
cccccatgca atttttttag tctcttcatt ctctcaacta aaactagatt tgcttcttat  60
agtttcttgt ccatgtctct tctcattcat acttgaagta gtacaataac aagaaaataa 120
```

| catttagcc | atg | gat | tgt | ata | gat | caa | gaa | caa | caa | caa | caa | caa | cca | gtt | 171 |
|---|---|---|---|---|---|---|---|---|---|---|---|---|---|---|---|
| | Met | Asp | Cys | Ile | Asp | Gln | Glu | Gln | Gln | Gln | Gln | Gln | Pro | Val | |
| | 1 | | | | 5 | | | | | 10 | | | | | |

| ttt | aag | cat | tat | tgt | aga | gtt | tgc | aag | aaa | ggt | ttt | gtg | tgt | ggg | aga | 219 |
|---|---|---|---|---|---|---|---|---|---|---|---|---|---|---|---|---|
| Phe | Lys | His | Tyr | <u>Cys</u> | <u>Arg</u> | <u>Val</u> | <u>Cys</u> | <u>Lys</u> | <u>Lys</u> | <u>Gly</u> | <u>Phe</u> | <u>Val</u> | <u>Cys</u> | <u>Gly</u> | <u>Arg</u> | |
| 15 | | | | | 20 | | | | | 25 | | | | | 30 | |

| gct | cta | ggt | ggg | cat | atg | aga | gct | cat | gga | att | ggg | gat | gaa | gtt | gta | 267 |
|---|---|---|---|---|---|---|---|---|---|---|---|---|---|---|---|---|
| <u>Ala</u> | <u>Leu</u> | <u>Gly</u> | <u>Gly</u> | <u>His</u> | <u>Met</u> | <u>Arg</u> | <u>Ala</u> | <u>His</u> | Gly | Ile | Gly | Asp | Glu | Val | Val | |
| | | | | 35 | | | | | 40 | | | | | 45 | | |

| act | atg | gat | gat | gat | gat | caa | gca | agt | gat | tgg | gaa | gat | aag | ttt | gga | 315 |
|---|---|---|---|---|---|---|---|---|---|---|---|---|---|---|---|---|
| Thr | Met | Asp | Asp | Asp | Asp | Gln | Ala | Ser | Asp | Trp | Glu | Asp | Lys | Phe | Gly | |
| | | 50 | | | | | 55 | | | | | 60 | | | | |

| ggg | agt | gtt | aag | gaa | ggt | aat | aaa | agg | atg | tac | caa | tta | aga | aca | aac | 363 |
|---|---|---|---|---|---|---|---|---|---|---|---|---|---|---|---|---|
| Gly | Ser | Val | Lys | Glu | Gly | Asn | Lys | Arg | Met | Tyr | Gln | Leu | Arg | Thr | Asn | |
| | | 65 | | | | | 70 | | | | | 75 | | | | |

| cct | aat | agg | caa | aaa | agc | aat | aga | gtt | tgt | gag | aat | tgt | ggg | aaa | gaa | 411 |
|---|---|---|---|---|---|---|---|---|---|---|---|---|---|---|---|---|
| Pro | Asn | Arg | Gln | Lys | Ser | Asn | Arg | Val | <u>Cys</u> | <u>Glu</u> | <u>Asn</u> | <u>Cys</u> | <u>Gly</u> | <u>Lys</u> | <u>Glu</u> | |
| | 80 | | | | | 85 | | | | | 90 | | | | | |

| ttc | tct | tct | tgg | aaa | tct | ttt | ctt | gaa | cat | gga | aaa | tgt | agc | tca | gaa | 459 |
|---|---|---|---|---|---|---|---|---|---|---|---|---|---|---|---|---|
| <u>Phe</u> | <u>Ser</u> | <u>Ser</u> | <u>Trp</u> | <u>Lys</u> | <u>Ser</u> | <u>Phe</u> | <u>Leu</u> | <u>Glu</u> | <u>His</u> | <u>Gly</u> | <u>Lys</u> | <u>Cys</u> | Ser | Ser | Glu | |
| 95 | | | | | 100 | | | | | 105 | | | | | 110 | |

| gat | gca | gaa | gag | tct | tta | gta | tcc | tcg | ccc | ggt | tca | gag | ggc | gag | gat | 507 |
|---|---|---|---|---|---|---|---|---|---|---|---|---|---|---|---|---|
| Asp | Ala | Glu | Glu | Ser | Leu | Val | Ser | Ser | Pro | Gly | Ser | Glu | Gly | Glu | Asp | |
| | | | | 115 | | | | | 120 | | | | | 125 | | |

| tac | att | tat | gat | gga | aga | aaa | gaa | aaa | gga | tac | gga | tgg | tct | aaa | aga | 555 |
|---|---|---|---|---|---|---|---|---|---|---|---|---|---|---|---|---|
| Tyr | Ile | Tyr | Asp | Gly | Arg | Lys | Glu | Lys | Gly | Tyr | Gly | Trp | Ser | Lys | Arg | |
| | | | 130 | | | | | 135 | | | | | 140 | | | |

FIG. 3 (Continued)

```
aag agg tca tta aga aca aaa gta gga ggc ctt agt act tca act tat    603
Lys Arg Ser Leu Arg Thr Lys Val Gly Gly Leu Ser Thr Ser Thr Tyr
        145                 150                 155 caa tca agt gag gaa gaa gat ctt ctc ctt gca aaa tgc ctt ata gat    651
Gln Ser Ser Glu Glu Glu Asp Leu Leu Leu Ala Lys Cys Leu Ile Asp
        160                 165                 170 tta gcc aat gca agg gtt gat aca tca ttg gtt gag cca gaa gag tct    699
Leu Ala Asn Ala Arg Val Asp Thr Ser Leu Val Glu Pro Glu Glu Ser
175                 180                 185                 190 tgt gcc tca gcc agt agg gag gag gaa cgg gcg gca cgg aac tcg atg    747
Cys Ala Ser Ala Ser Arg Glu Glu Glu Arg Ala Ala Arg Asn Ser Met
                195                 200                 205 gcc tac ggc ttc acc cca tta gtg agt act cgt gta ccc ttt gac aac    795
Ala Tyr Gly Phe Thr Pro Leu Val Ser Thr Arg Val Pro Phe Asp Asn
                210                 215                 220 aag gct aaa ggg gcg tct agt aaa ggg ttg ttt gaa tgt aaa gct tgc    843
Lys Ala Lys Gly Ala Ser Ser Lys Gly Leu Phe Glu Cys Lys Ala Cys
                225                 230                 235 aag aaa gtc ttc aat tcc cac caa gcc cta ggt gga cat agg gca agt    891
Lys Lys Val Phe Asn Ser His Gln Ala Leu Gly Gly His Arg Ala Ser
        240                 245                 250 cac aag aaa gtt aag ggg tgt tat gca gcg aag caa gat caa ctc gat    939
His Lys Lys Val Lys Gly Cys Tyr Ala Ala Lys Gln Asp Gln Leu Asp
255                 260                 265                 270 gat atc tta att gat gat caa gat gtg aat atc aca cat gat caa gaa    987
Asp Ile Leu Ile Asp Asp Gln Asp Val Asn Ile Thr His Asp Gln Glu
                275                 280                 285 ttc ctg caa agt tca aaa tcc atg agg aag tca aaa atc cat gaa tgc    1035
Phe Leu Gln Ser Ser Lys Ser Met Arg Lys Ser Lys Ile His Glu Cys
                290                 295                 300
```

FIG. 3 (Continued)

```
tca ata tgc cat aga gtt ttc tcg aca gga caa gct tta ggt ggt cac   1083
Ser Ile Cys His Arg Val Phe Ser Thr Gly Gln Ala Leu Gly Gly His
    305                 310                 315 aag agg tgc cac tgg atc acc tcc aat tcc ccc gat tct tcg aaa ttt   1131
Lys Arg Cys His Trp Ile Thr Ser Asn Ser Pro Asp Ser Ser Lys Phe
    320                 325                 330 cat ttc aat ggt cat gtg gag caa att aat cta aga tca aac atg cat   1179
His Phe Asn Gly His Val Glu Gln Ile Asn Leu Arg Ser Asn Met His
    335                 340                 345                 350 aaa tca gat gca tta gat ctt aat aac ctt ccg aca cat gaa gac atg   1227
Lys Ser Asp Ala Leu Asp Leu Asn Asn Leu Pro Thr His Glu Asp Met
                355                 360                 365 tcg cga att aga cga gac ccc ttt aat cca tta agc ttc gag gtg tca   1275
Ser Arg Ile Arg Arg Asp Pro Phe Asn Pro Leu Ser Phe Glu Val Ser
            370                 375                 380 aca gat ata cac ttg caa tat cca tgg agt tgt gct cca aaa aat gat   1323
Thr Asp Ile His Leu Gln Tyr Pro Trp Ser Cys Ala Pro Lys Asn Asp
        385                 390                 395 gat aat gac aat tac tac ctt gaa gaa att aaa atc gat agt aat gcc   1371
Asp Asn Asp Asn Tyr Tyr Leu Glu Glu Ile Lys Ile Asp Ser Asn Ala
    400                 405                 410 aac aac ggt aag tac aat att aat aat ggt gca aca caa aat gta gaa   1419
Asn Asn Gly Lys Tyr Asn Ile Asn Asn Gly Ala Thr Gln Asn Val Glu
415                 420                 425                 430 gat gat gaa gca gat agt aaa ttg aag tta gct aag cta agt gac cta   1467
Asp Asp Glu Ala Asp Ser Lys Leu Lys Leu Ala Lys Leu Ser Asp Leu
                435                 440                 445 aag gat atg aat acc aac tct gat aat ccc gcc cat tgg tta caa gtt   1515
Lys Asp Met Asn Thr Asn Ser Asp Asn Pro Ala His Trp Leu Gln Val
        450                 455                 460
```

FIG. 3 (Continued)

```
ggg att ggt tca act aca gaa gta ggg gct gat tca taa gtaactatat   1564
Gly Ile Gly Ser Thr Thr Glu Val Gly Ala Asp Ser
        465                 470                 475 gcagttattc ctttgcttaa tttctttttt ttctgtcacc cgagtatata tttatatgca 1624
aatattgtaa ttataacttc accaaacaga tagtaactgt ttggtgatgc aaatactgtt 1684
aatatttgta ctccctttt  ttttgtcctt ttcttgtaat tgatacacaa tcttgtaatt 1744
ttttgtactt tcaatttctt gagctgtaat tttcagtgta atacagaact cagaatatgt 1804
tattcttgca atatgaagtt tagtatgcaa cagtcaaaca cgattagtag aagtggtctg 1864
taatccctcc cactagttac aagttgggat tgattcaccc acagtagttg gggctgactt 1924
tgaagtaaac atatgcagtt attc                                       1948
```

FIG. 4
(a)
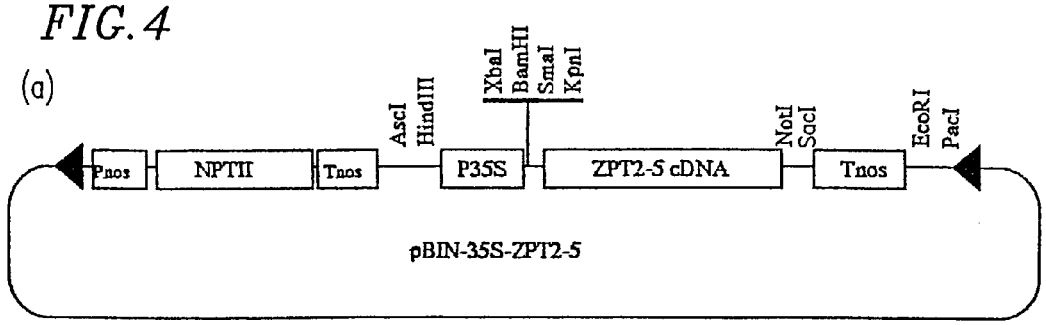
(b)
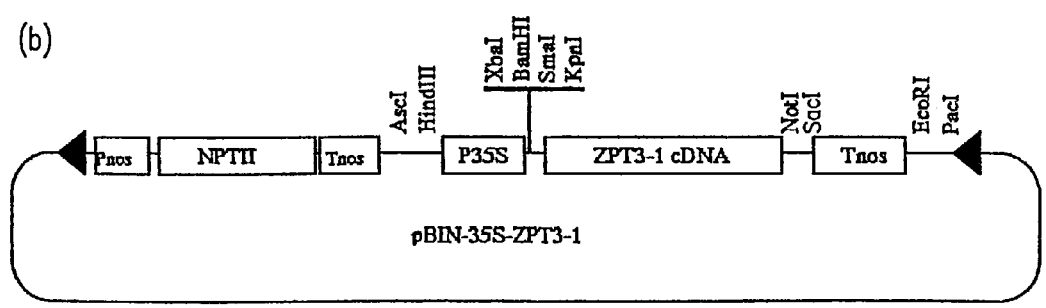
(c)
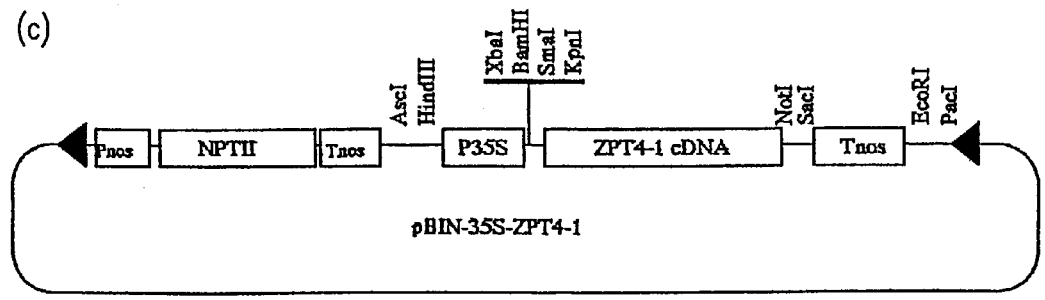

FIG. 5

```
ctgcaggcag caacattagg agattttcca gcaccaatct ccctatgtgc tataacttca 60
cttataggca tggtattgac tggaattgta caattgatac aacaagggtc gttggagatt 120
ggattgcccc tgttaagcat ccgtgactta ataggctact cgttattggt aattcatcaa 180
atatccctga aattctcaca ttaattatgt taatacagaa attctgagtt agatttgact 240
tacatacgtt gatagcctaa ataatttgta tgatactaac gtttttttaa cctgatactt 300
tatattaact ttgaggtttg tctaattttt tgtggttatc ataggcaggt atagttagtg 360
gagcatgtgt aagtttcaat aattgggcaa tgaagaaaag agggccagtc ttagtttccg 420
tatttagtcc tgttggaact gtgataactg tcgtactttc tgctatcacc ttgaagtaca 480
caattactat gggaaggtaa aaccttatcc attttcactt ggatctagct tatatacagt 540
gtaaagaaat ttttacaata ttttccaagt aacttttaaa gacgattatc aataatcatg 600
ttttacttaa cctgatagtg taaatatatt ttttcacact tacaattact ttagttcttt 660
ttcagttgca tcaaaattca aacttcaaat gacttaactt ctttttgcag ccttggtggt 720
atgtttctca tgtttacggg tctgtatttc gtgttatggg ctaaaaggaa cgaaggattt 780
ctaaataata ccaactcctc agaaagtgag tacgatgttg agaagcctct tttgcattaa 840
atttctttt attctcaatt gtaatatgta gttagtttgt atatacaact agaatccaac 900
atagagaaga gagagggaga gcttgtttgt accaaataga taacatgtat gttgatttaa 960
gtatcccata ttggtactgg aagtanactg ttaatgttgc ctgcgattca attgtccagt 1020
ccttggtgta gtgagacagt gttaaatatc ccacatggta taaaaaatgg attgctgtct 1080
ccttatatgg tatttgacaa toctcacatt ttgagctaaa atttggggttg agttaatgca 1140
attgtccatt tcttatcaat gtatttaatc taggcttgga gctaaaaata caaagcaaaa 1200
gagaagagag aaaaagaaca aagaaagact attatgatag ttgatatttg aaaaaatgca 1260
agttccaatc ctagtaatat ctttttatttt gcagtagcat gacggaatat gggaatcaac 1320
atgtagctgc ttttctggct ctatctaagc ccctcttctt ttaccatagt tttgttttc 1380
attcactttt ggaagcagca agggtagatt tagaccacaa atatgcaaat gttttttttt 1440
tttttttttt tgtaaagtct tagacctata tggagtataa cctttgggaa aggggattga 1500
atcaatgatc ataatgtcac aatcatgtag tactacattt tttgttcttc aatttgagct 1560
actagtttga catttcccaa gtaaattatg cttcaacact aggattctct tgtttatatt 1620
atctcattga agctatgctt taactctctt ccttgagtgg attaacttga aaaagtaggc 1680
aaagaaattt atgagagttc tgatatcgat atcatagagg acacaaaatt aagaaaatgc 1740
gaaaagactt atacccaaca aagaaaatat gaacactagt atcgatcacc acccagattt 1800
acaatttaat gtactggtgt tcaattttgt gcttgcatcg actatttcac cgaatattta 1860
ttcttattta taaaaatatc gaataactat gaccatcaaa gtttagccaa ataaaatata 1920
aaaagtatc tatatcacta tagtaaactt tgtatttatt ggaattgaac tcacacttct 1980
tccattacta cgtcaaatcc cagaaggcat attataagtt tttgtttcaa agcctccaaa 2040
ccaagtacac tcatttctct tttgaagaaa gcgagttcat ttgtaggcta cgtgaatata 2100
actactttaa aatattgctt tgtttcgaat ttgccatgag ttactacatt cacacaaaat 2160
tcttaatgcg actcagagtg tgtgttttaa ttttcttttta gagtgtttgt acttctatat 2220
gagggtcact agtaaagtag tccactaata ttacaaattc ttacattacg tacaatgtga 2280
```

FIG. 5 (Continued)

```
ttttatgtca gtagatttga ctgaatgcta taactacgag agttagaaat agtctttgcc 2340
aaccacatta taaactgacc ctccacttgt cataacaaac tctcttgttc tcatccacaa 2400
ctaactttaa ctagaaacta ggacttccct cacttatgct acaaaaatcc ttataactac 2460
accacaacct ttagtactgt tcactaacta attctttatt tataccaacc ctggcttgga 2520
gtgtagcaaa aaaatgtaca ctactccaaa gtaaacacta ttctttgaaa ctttccttgt 2580
tgcactttaa tttatgttct agtgagtata ttagagagtg agaaatggtg gacaatagcc 2640
agaaaaatga accatcaact gttatacact attgtagagt atgtaaaagg ggatttaata 2700
ngtntggagc tc                                                    2712
```

FIG. 6

```
gaattcacca ccacgagtac ttattttgat gagcatggca ttattttca aacttcttgt 60
gctggaacac cacagcagaa cgggaaagtt gagcgaaaac ataaacatat tttgaatgtt 120
gctcgagcac ttaggtttca agcgcatttc ccaattgagt tttggggtga gtgtgttttg 180
atggcgtgct atttgatcaa gcgaaccctc tcatcggtct tacacagaaa aaaatgccat 240
atgatgtctt ttttggtgta acaccgaact acgagcattt gaaagtgttt ggatctctat 300
gctatggtca caagcatggg tgcttgggag ataagtttga aagtaggagt cgtctgtgtg 360
tttttattgg atacccatat gggaagaaat catggaagtt atatgatttg gacaccaaaa 420
aatattttgt gtcgcgggca cctagcaccg aagcactaag catccgaacc caacgttatt 480
tcagcctatg agagtgattg aagatgacta tggtattgaa gtgagggggt agtgacactg 540
ttttgacaca aaaaccgaac aaggagagga tacagctcga ggacgtgata attgacactc 600
caagtttggc tacagagact aatgtcatgg aagtagaaaa cccggtcacc ggtgtcatgt 660
ccgatcaatt gaangctgaa gctgtgggag aagagttggg tcgagaaaac taattaggaa 720
ggagaatgtc tccttcgtga tttttcactg gtctgtcgaa aggttagtca ccaggtttca 780
acctgtgtcc acatgtctga tttctcaccc gtgacacaac gagcctcagg tacgccttat 840
cctcttacac actatgttaa ttgtgaccgt ttttcttcga agcatgtgag ttttcttgca 900
gctattacgg agggtcgtga atcgacctct ttctgtgtgg ccataaagaa tgaaaaatgg 960
agaaagacta tgcaatagga gtttcaagca ttggaagata ataaaacatc tatggttggt 1020
tacttgccac ctgggaagaa agcgctcgga tgtcggtggg tgtataagat caaatataat 1080
tccgatggat cagtggtacg atacaaggca cgtttggtta gttttggaaa tcatcaggtc 1140
aaaggcattg attatacgta gacatttgct ccagtcgcta aaatagtgac tttgaggaca 1200
tttcttgcag tcgctgcagc taaaaattgg gaattgcatc aaatggatgt tcataatgca 1260
tttgtacagg tgatcttcat gaaaaagtct atatgaagct gccaccaagg tatcagacta 1320
atggttacgg taatgtgtgt cgcctatgaa agttttgta tggtttgaag caggcgtcga 1380
gatgttggtt cacgaagtta ttggccgatt tgaaaactta tgcttttana caatcttatt 1440
cggattattg ccttttaca cttcgtaaag ggtccgtcac cttaagtgtg ttggtgtacg 1500
tggatgattt gattattggg gcaataattc ggaagctatt cgtctcttta agttgtatct 1560
ctccacttgc tttcttatga aagatttggg catactaaat ttttggggag atgaagtggc 1620
tagaggacct aaaggtattt tcctatgtca atggaaatat gccttggata taattggatt 1680
attaggagct cgactggttg gaacttctat ggagcagaat catcgtttgg ctttggcaag 1740
tggccgatat attgatgatc tacatagata tatttgattg atgattctag tgcttaatta 1800
aagactgatc aattgtactg ttattaatta atctttgttt aggaggagca tgtgggctgg 1860
aaaatgatgt agcaaacttt ccatacaatg ccatgattac tgcaggaaat gaagtcctat 1920
ttaaacatgg ctttggctgt ggtgcatgct accaggtgca cttgaaattt gttttataaa 1980
aagagaaaca catgcatgaa ttttgagttt cacttcgcaa aataaatgaa atctttattt 2040
atattaatgc aatcgatttt caggtgttgt gcttacagaa tcaaaatcaa tactgctcag 2100
gaaatccaat aatagtaact nttacagatg agtgcccagg ggcatgcaat aatgatcctg 2160
ttcattttga ttttagtgga actgcttttg gagccttggc aaaacctggc caagctgaac 2220
aattgcgtaa tgaaggaaga atccaaatta attacagaag gtgagttacg ttccacatga 2280
```

FIG. 6 (Continued)

```
caaatagaga aatcaataca aaatttccat ttacttagta acactctttc cttgttagta 2340
tgcctaaaaa agagtagtac acaacacaat taatgcacaa ttttgctaaa ccatgatatt 2400
gaatcgtgca gagtggcatg cagttacaag gcaaatatac aatttaaggt agacaaaggc 2460
tccaatcctg atttcttggc agttgcagct gaggcagtta atggagatgg tgatctttct 2520
tttgtagaaa ttaaagcatc caattcgaat caatggcttc ccatgcaaca aatgtttggg 2580
gcaacttgga gcgttggcat caagccagac acacagaaac ctcctttctc acttagactt 2640
actacagaat ttaagcaaac agtcattgcc caaaatgtca taccagtggg ttggcaacca 2700
agagcaattt acaaatcaaa tgtcaatttc ccacccaagc tttagtttaa tcttttacc 2760
cacaatagtg taaaaataat tataaggact acaaattaaa tactctatgt tcaacagtgc 2820
tatttaatta taataaggat tacaaattaa agtgaggatt cttctcaatg ataatgtcaa 2880
aagtttggga tgtcaaatct atttgtattt tttttcacat caatgatcaa tgaaagttat 2940
gcttttagta tttttttaatt attaataatt tgttttcatg tatttcaata ataatattat 3000
ctcaaaagta aataaatcaa tattcaaaac tgacatgaaa attttcattc tcactatatt 3060
tatgttcttt tttcagtctc aaacgcccaa attttgtacg aaaaaattgt tcggataagc 3120
gagaaacact cataactgat aaaaacagaa tagtgaataa agaaaactaa atatatttac 3180
tcttgatgag tccatgatgt gtaagtatta tcttctgccg tccaatttgg ttgtttgaca 3240
ccactagtgt tattaataaa aagtttgtga aaaaataagc tcttcactcc cttaggcctt 3300
actctctcct tccacttgtc atactcactc ttcacttcca ctcacactcc tatttttctc 3360
tttacctcta aactctcctc cacaaaccac tacttcaact aaaaactagg actaattttt 3420
ttctcaccgt acaagtccac aacaacttct agtacaagaa caaacaaact ctcgttgtgc 3480
ccctcgctcc catgcatgca cacccccatg caattttttt agtctcttca ttctctcaac 3540
taaaactaga tttgcttctt atagtttctt gtccatgtct cttctcattc atacttgaag 3600
tagtacaata acaagaaaat aacatttagc catggattgt atagatcaag aacaacaaca 3660
acaacaacca gttttttaagc attattgtag agtttgcaag aaaggttttg tgtgtgggag 3720
agctctaggt gggcatatga gagctcatgg aattggggat gaagttgtaa ctatggatga 3780
tgatgatcaa gcaagtgatt gggaagataa gtttggaggg agtgttaagg aaggtaataa 3840
aaggatgtac caattaagaa caaaccctaa taggcaaaaa agcaatagag tttgtgagaa 3900
ttgtgggaaa gaattcctgc agcccggggg atccactagt tctagagcng ngcgcaccgc 3960
ggtggagctc cagcttttgt tccctttacg tgagggttaa tt                     4002
```

FIG. 7
(a)
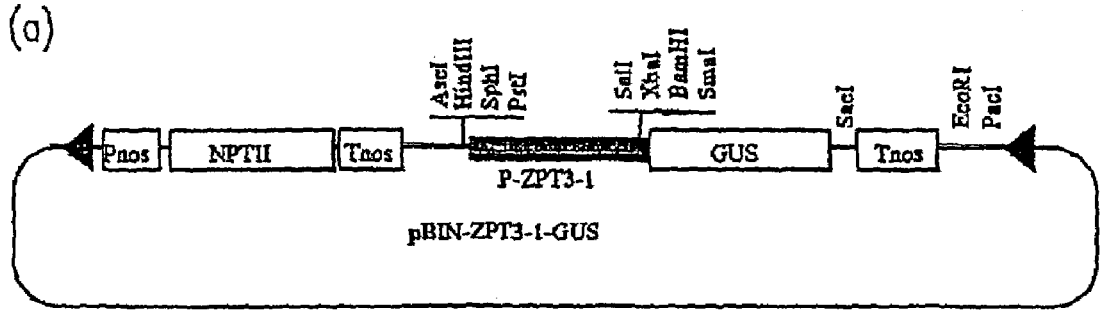
(b)
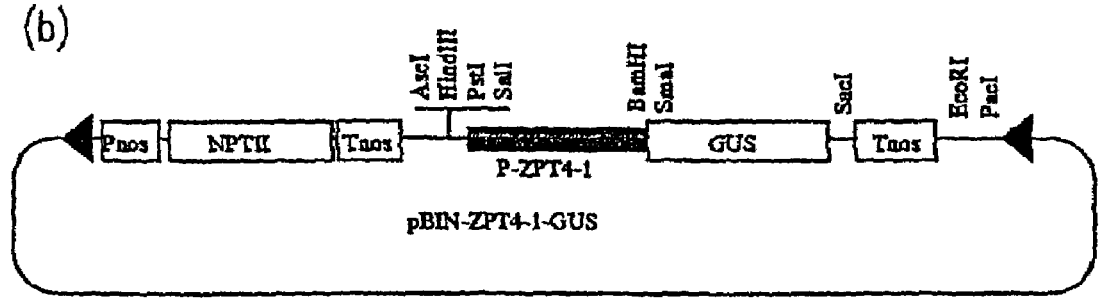

Anther    Anther (High Magnification)

US 6,989,473 B1

METHOD OF MAKING MALE STERILE *PETUNIA* PLANTS BY TRANSFORMATION WITH A NUCLEIC ACID ENCODING A ZINC FINGER TRANSCRIPTIONAL FACTOR

This application claims priority to application no. PCT/JP99/06467 filed 19 Nov. 1999, now publication no. WO 01/37643 published 31 May 2001 which is incorporated herein by reference.

TECHNICAL FIELD

The present invention relates to genes which are expressed specifically in the pollen producing tissues of stamens and use of the same. More particularly, the present invention relates to the genes for zinc finger transcription factors (ZPT2-5, ZPT3-1 and ZPT4-1) derived from *Petunia*, are expressed specifically in microspores, and use of the same.

BACKGROUND ART

Pollen fertility causes problems in various aspects of agriculture and horticulture. For example, in the case of mating for cross breeding, self-pollination has to be avoided by castration (removal of stamens) which requires enormous effort. In the seed and seedling industry, there is a demand for a trait of lack of pollen fertility from the standpoint of commercially protecting excellent breeds obtained by cross breeding. To meet such a demand, a technique for controlling pollen fertility (pollination control) has been strongly required. Conventionally, for particular crops, lines of cytoplasmic male sterility have been used for cross breeding, and some success has been achieved. However, the cytoplasmic sterility trait is often accompanied by undesired side effects, such as a reduction in disease resistance and the like. There are further problems, such as that the trait is unstable, that it is difficult to mass-produce the seeds, and the like. A method for reducing the fertility by treating with a chemical agent(s) has been studied, but safety evaluation and elucidation of the mechanism of this method have not been fully done and thus such a method is not yet in actual use. Therefore, there is a demand for an excellent male sterilization technique using genetic engineering.

Pollen is the male gametophyte of spermatophyte. The development of pollen which proceeds while pollen is surrounded by an anther as a supporting tissue is divided into the following stages: the tetrad stage immediately after the meiosis of microsporogenous cells (pollen mother cells); the release stage during which microspores are released from the tetrad; the uninucleate stage characterized by the enlargement and vacuolation of pollen cells, the mitotic stage giving rise to the differentiation into vegetative and generative cells by mitosis; and the subsequent binucleate stage. After these stages, the anther finally dehisces and matured pollen grains are released. Therefore, it can be said that the microspore is one of target tissues which are most suitable for artificial control in order to inhibit the development of pollen and eliminates pollen fertility.

As described above, great expectations are placed on male sterilization techniques using genetic engineering. Particularly, if a gene which is expressed specifically in the direct precursor of a pollen cell, such as a microspore, can be utilized, it is considered to be highly likely that male sterilization can be achieved without conferring undesired traits to plants. Several examples of promoters specific to various stamen tissues and gene constructs for male sterilization comprising the promoter have been reported (Shivanna and Sawhney Ed., Pollen biotechnology for crop production and improvement (Cambridge University Press), pp. 237–257, 1997). However, there has been continuously a demand for a novel gene useful for control of pollen fertility, which has high tissue and temporal specificities of expression.

Recently, the inventors of the present application specified the cDNA sequences of novel transcription factors derived from *Petunia*, i.e., seven zinc finger (ZF) transcription factors including PEThy ZPT2-5, PEThy ZPT3-1, and PEThy ZPT4-1 (hereinafter abbreviated as ZPT2-5, ZPT3-1, and ZPT4-1, respectively). And the inventors reported that Northern blot analysis indicates that each transcription factor transiently expresses in an anther-specific manner in a different stage of the development of the anther (Kobayashi et al., Plant J., 13:571, 1998). However, the physiological function and action of these transcription factors in plants, and the precise expression sites and the expression controlling mechanism of the genes encoding the transcription factors have been not clarified.

DISCLOSURE OF THE INVENTION

The objective of the present invention is to provide a genetic engineering technique using a pollen-specific gene which is useful for modification of a plant trait, representatively male sterility.

The present inventors reintroduced genes encoding anther-specific transcription factors (ZPT2-5, ZPT3-1 and ZPT4-1), which had been previously isolated from *Petunia*, into *Petunia*. As a result, it was found that the normal development of pollen was inhibited, so that pollen fertility was significantly reduced (ZPT2-5 and ZPT4-1), or substantially eliminated (ZPT3-1). Further, the inventors isolated upstream regions of the ZPT3-1 and ZPT4-1 genomic genes, respectively, and studied the tissue specificity of the promoter activity. As a result, it was found that the promoter activity is expressed in microspores from the uninucleate stage to the binucleate stage in a tissue and temporal-specific manner. The present invention was completed based on these findings.

According to a first aspect of the present invention, a method for producing a male sterile plant comprises the steps of providing a plant expression cassette including: a nucleic acid being any of (i) DNA having a sequence from position 1 to position 777 of a base sequence indicated by SEQ ID NO: 1, (ii) DNA hybridizing the DNA having the base sequence (i) under stringent conditions and encoding a transcription factor controlling the development of pollen, and (iii) a DNA fragment of (i) or (ii); and a promoter operatively linked to the nucleic acid, providing plant cells having an endogenous transcription factor controlling the development of pollen, wherein a gene encoding the endogenous transcription factor hybridizes the nucleic acid under stringent conditions, introducing the expression cassette into the plant cells, regenerating the plant cells, into which the expression cassette has been introduced, to plants; and screening the regenerated plants for one in which the nucleic acid is expressed so that expression of the endogenous transcription factor is suppressed.

According to a second aspect of the present invention, a method for producing a male sterile plant comprises the steps of providing a plant expression cassette including: a nucleic acid being any of (i') DNA having a sequence from position 1 to position 1640 of a base sequence indicated by SEQ ID NO: 3, (ii') DNA hybridizing the DNA having the base sequence (i') under stringent conditions and encoding a transcription factor controlling the development of pollen, and (iii') a DNA fragment of (i') or (ii'); and a promoter operatively linked to the nucleic acid, providing plant cells having an endogenous transcription factor controlling the development of pollen, wherein a gene encoding the endogenous transcription factor hybridizes the nucleic acid under stringent conditions, introducing the expression cassette into the plant cells, regenerating the plant cells, into which the expression cassette has been introduced, to plants; and screening the regenerated plants for one in which the nucleic acid is expressed so that expression of the endogenous transcription factor is suppressed.

According to a third aspect of the present invention, a method for producing a male sterile plant comprises the steps of providing a plant expression cassette including: a nucleic acid being any of (i") DNA having a sequence from position 1 to position 1948 of a base sequence indicated by SEQ ID NO: 5, (ii") DNA hybridizing the DNA having the base sequence (i") under stringent conditions and encoding a transcription factor controlling the development of pollen, and (iii") a DNA fragment of (i") or (ii"); and a promoter operatively linked to the nucleic acid, providing plant cells having an endogenous transcription factor controlling the development of pollen, wherein a gene encoding the endogenous transcription factor hybridizes the nucleic acid under stringent conditions, introducing the expression cassette into the plant cells, regenerating the plant cells, into which the expression cassette has been introduced, to plants; and screening the regenerated plants for one in which the nucleic acid is expressed so that expression of the endogenous transcription factor is suppressed.

It should be noted that the DNAs of (ii), (ii') and (ii") each do not include (iv) DNA hybridizing DNA having a sequence from position 1 to position 1886 of abase sequence indicated by SEQ ID NO: 13 under stringent conditions and encoding a transcription factor controlling the development of pollen. The base sequence indicated by SEQ ID NO: 13 is a cDNA sequence encoding another transcription factor ZPT3-2 isolated from *Petunia* (Kobayashi et al. above).

The method according to the first through third aspects of the present invention is utilized as a method for conferring male sterility to a plant.

In one embodiment of the first through third aspects, the nucleic acid is linked in a forward direction with respect to the promoter, and may be transcribed in a sense direction in cells of the plant.

In one embodiment of the first through third aspects, the nucleic acid is linked in a reverse direction with respect to the promoter, and may be transcribed in a antisense direction in cells of the plant.

In one embodiment of the first through third aspects, the plant is dicotyledon. The dicotyledon is preferably of the family Solanaceae, and more preferably of the genus *Petunia*.

In one embodiment of the first through third aspects, the expression cassette is incorporated into a plant expression vector.

According to the first through third aspects of the present invention, a male sterile plant produced by a method according to any of the above-described methods is also provided.

According to a fourth aspect of the present invention, a method for producing a plant having a modified trait comprises the steps of providing a plant expression cassette including: a promoter including any of (a') DNA having a sequence from position 1 to position 2624 of a base sequence indicated by SEQ ID NO: 7 and (b') DNA having a part of the sequence of (a') and exhibiting promoter activity specific to microspores; and a heterologous gene operatively linked to the promoter, introducing the expression cassette into plant cells, and regenerating the plant cells, into which the expression cassette has been introduced, to plants.

According to a fifth aspect of the present invention, a method for producing a plant having a modified trait comprises the steps of providing a plant expression cassette including: a promoter including any of (a") DNA having a sequence from position 1 to position 3631 of a base sequence indicated by SEQ ID NO: 8 and (b") DNA having a part of the sequence of (a") and exhibiting promoter activity specific to microspores and optionally the dehiscence tissue of an anther; and a heterologous gene operatively linked to the promoter, introducing the expression cassette into plant cells, and regenerating the plant cells, into which the expression cassette has been introduced, to plants.

In one embodiment of the fourth and fifth aspects, the trait is fertility, and the plant having a modified trait is a male sterile plant. Therefore, the method of the present invention may be utilized as a method for conferring male sterility to a plant.

In one embodiment of the fourth and fifth aspects, the trait is compatibility, and the plant having a modified trait is a self-incompatibile plant. Therefore, the method of the present invention may be utilized as a method for conferring self-incompatibility to a plant.

In one embodiment of the fourth and fifth aspects, the plant is dicotyledon. The dicotyledon is preferably of the family Solanaceae, and more preferably of the genus *Petunia*.

In one embodiment of the fourth and fifth aspects, the expression cassette is incorporated into a plant expression vector.

In one embodiment of the fourth and fifth aspects, a trait-modified plant produced by a method according to any of the above-described methods is provided.

According to a sixth aspect of the present invention, a promoter comprises DNA of the following (I') or (II'): (I') DNA having a sequence from position 1 to position 2624 of a base sequence indicated by SEQ ID NO: 7; and (II') DNA having a part of the sequence of (I') and exhibiting promoter activity specific to microspores.

According to a seventh aspect of the present invention, a promoter comprises DNA of the following (I") or (II"): (I") DNA having a sequence from position 1 to position 3631 of a base sequence indicated by SEQ ID NO: 8; and (II") DNA having a part of the sequence of (I") and exhibiting promoter activity specific to microspores and optionally the dehiscence tissue of an anther.

According to an eighth aspect of the present invention, a plant expression cassette useful for conferring male sterility to a plant, comprising any of the above-described microspore-specific promoters and a heterologous gene operatively linked to the promoter.

BRIEF DESCRIPTION OF THE DRAWINGS

FIG. 1 is a diagram showing a cDNA sequence of a gene encoding ZPT2-5 (herein also simply referred to as "ZPT2-5 gene") (SEQ ID NO: 1) and the corresponding amino acid sequence (SEQ ID NO: 2). Two zinc finger motifs and a DLNL sequence (amino acids from position 145 to position 155) are underlined.

FIG. 2 is a diagram showing a cDNA sequence of a gene encoding ZPT3-1 (herein also simply referred to as "ZPT3-1 gene") (SEQ ID NO: 3) and the corresponding amino acid sequence (SEQ ID NO: 4). Three zinc finger motifs and a DLNL sequence (amino acids from position 408 to position 417) are underlined.

FIG. 3 is a diagram showing a cDNA sequence of a gene encoding ZPT4-1 (herein also simply referred to as "ZPT4-1 gene") (SEQ ID NO: 5) and the corresponding amino acid sequence (SEQ ID NO: 6). Four zinc finger motifs and a DLNL sequence (amino acids from position 438 to position 449) are underlined.

FIG. 4 is a schematic diagram showing structures of plant expression vectors used for expression of each cDNA sequence of ZPT2-5, ZPT3-1 and ZPT4-1 (pBIN-35S-ZPT2-5, pBIN-35S-ZPT3-1 and pBIN-35S-ZPT4-1).

FIG. 5 is a diagram showing an upstream sequence of the coding region of the ZPT3-1 gene (SEQ ID NO: 7). The transcription initiation site is indicated by a thick arrow (position 2567). The translation initiating codon (ATG) is indicated by a thick underline.

FIG. 6 is a diagram showing an upstream sequence of the coding region of the ZPT4-1 gene (SEQ ID NO: 8). The transcription initiation site is indicated by a thick arrow (position 3503). The translation initiating codon (ATG) is indicated by a thick underline.

FIG. 7 is a schematic diagram showing structures of plant expression vectors for analyzing promoters for the ZPT3-1 and ZPT4-1 genes (pBIN-ZPT3-1-GUS and pBIN-ZPT3-1-GUS).

FIGS. 8(*a*) through (*d*) are of the wild-type *Petunia* and FIGS. 8(*e*) through (*h*) are of the cosuppressed transformed *Petunia*, each of which shows the pollen of a bud at a different development stage. All the pollen were stained by a commonly used method using DAPI (4',6-diamidino-2-phenylindole dihydrochloride n-hydrate).

FIGS. 9(*a*) and (*c*) are of the wild-type *Petunia* and FIGS. 9(*b*) and (*d*) are of the transformed *Petunia*, each of which shows the pollen at the tetrad stage and the microspore stage, respectively. The pollen of the tetrad stage and the pollen of the microspore stage were stained by a commonly used method using DAPI and safranin, respectively. The pollen of the *Petunia* into which pBIN-35S— ZPT4-1 was introduced showed substantially the same form as FIGS. 9(*b*) and 9(*d*).

FIGS. 10(*a*) and (*d*) show the appearances of bud at the actual size. FIGS. 10(*b*) and (*e*) show the cross-sectional views of an anther at a low magnification (40 times). FIGS. 10(*c*) and (*f*) show the cross-sectional views of microspores (FIG. 10(*c*); the magnification is 700 times) and the dehiscence tissues and the surrounding vicinity of the anther (FIG. 10(*f*); the magnification is 200 times) at high magnification.

BEST MODE FOR CARRYING OUT THE INVENTION

Figure 8:
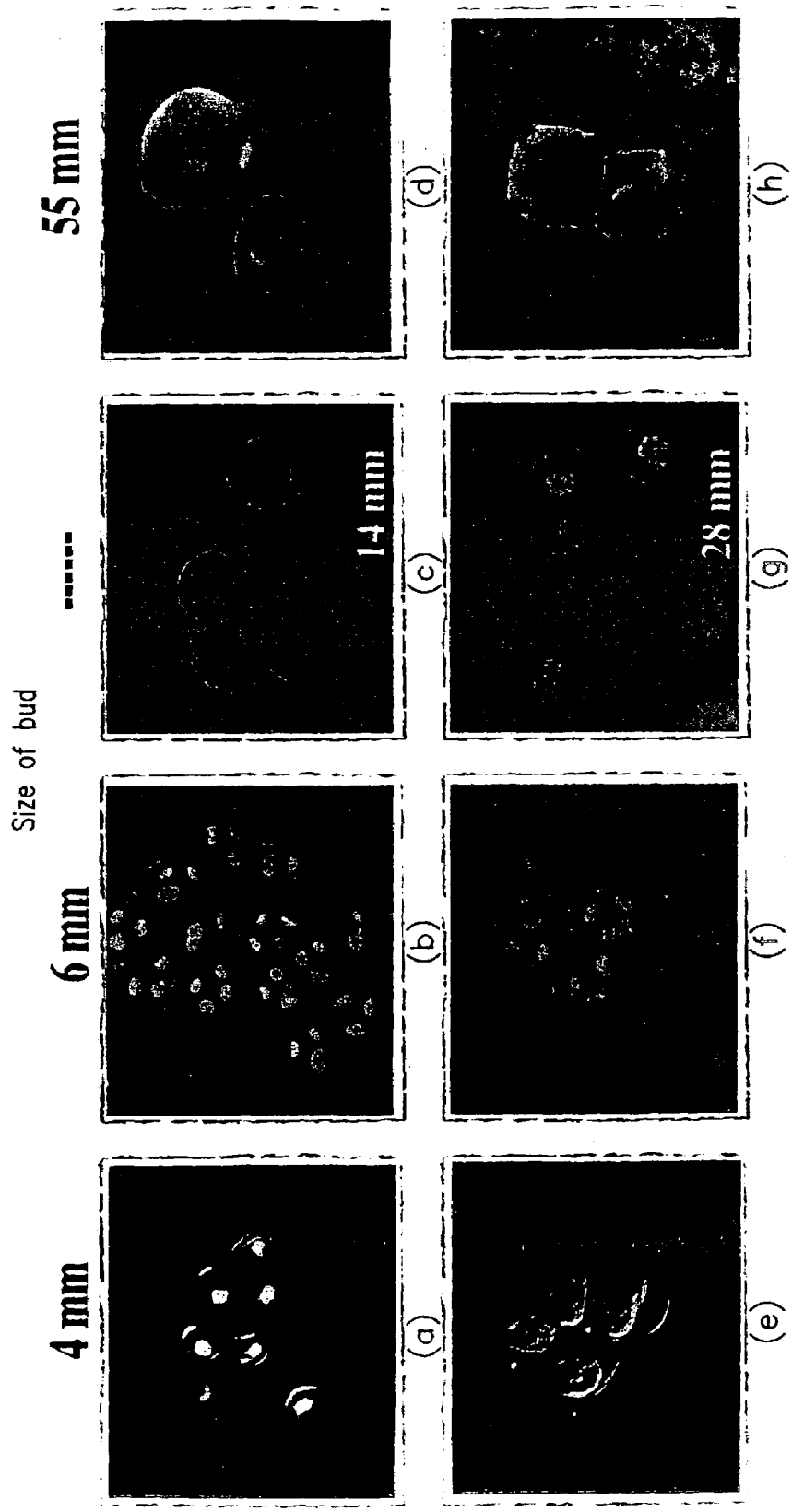
FIG. 8 shows photographs indicating the forms of organisms, i.e., the pollen of a wild type *Petunia* and the pollen of a *Petunia* into which pBIN-35 S-ZPT2-5 was introduced (a transformant in which cosuppression occurred) (the magnification is 400 times).

Hereinafter, the present invention will be described in detail.

(Transcription factors derived from ZPT2-5, ZPT3-1 and ZPT4-1 genes)

A nucleic acid, which is useful in a method for producing male sterile plants according to first to third aspects of the present invention, is any one of the following DNAs:
  (i) DNA having a sequence from position 1 to position 777 of a base sequence indicated by SEQ ID NO: 1;
  (i') DNA having a sequence from position 1 to position 1640 of a base sequence indicated by SEQ ID NO: 3:
  (i") DNA having a sequence from position 1 to position 1948 of a base sequence indicated by SEQ ID NO: 5,
  DNA which hybridizes to the DNA having any of the base sequences (i) to (i") under stringent conditions, and encodes a transcription factor which controls the development of pollen (i.e., (ii), (ii') or (ii")); or
  DNA which is a fragment of any of the above-described DNAs (i.e., (iii), (iii') or (iii")).

The above-described nucleic acid of the present invention is preferably DNA of (i), (i') or (i"), i.e., DNA encoding ZPT2-5, ZPT3-1 or ZPT4-1, or a fragment thereof, and more preferably DNA of (i), (i') or (i").

In the present specification, "transcription factor" refers to a protein for controlling the synthesis of mRNA by binding to DNA in the regulatory region of a gene. It is known that a certain type of transcription factor has a highly conserved amino acid sequence called a zinc finger (ZF) motif in the DNA binding domain. ZPT2-5 is a zinc finger (ZF) protein of the Cys2/His2 type (EPF family), which is a transcription factor which includes two ZF motifs in the full-length amino acid sequence consisting of 176 amino acids, and further, a hydrophobic region called a DLNL sequence. Similarly, ZPT3-1 is a ZF protein of the EPF family, which is a transcription factor which includes three ZF motifs in the full-length amino acid sequence consisting of 437 amino acids, and further, a DLNL sequence. Similarly, ZPT4-1 is a ZF protein of the EPF family, which is a transcription factor which includes four ZF motifs in the full-length amino acid sequence consisting of 474 amino acids, and further, a DLNL sequence. For any of the above-described transcription factors, see Kobayashi et al. (above). cDNA sequences (SEQ ID NO: 1, 3 and 5) encoding ZPT2-5, ZPT3-1 and ZPT4-1, respectively, are shown in FIGS. 1, 2 and 3 along with corresponding putative amino acid sequences (SEQ ID NO: 2, 4 and 6).

In the present specification, "fragment" of a nucleic acid or DNA refers to a fragment which can inhibit the expression of an endogenous transcription factor in a plant when the fragment is introduced into the plant and expressed in an appropriate manner. This fragment is selected from regions of DNAs of the above-described (i), (i'), (i"), (ii), (ii') or (ii") other than the regions encoding the zinc finger motifs in the DNAs. The fragment has a length of at least about 40 bases or more, preferably about 50 bases or more, more preferably about 70 bases or more, and even more preferably about 100 bases or more.

In the present specification, "stringent conditions" for hybridization are intended as conditions sufficient for the formation of a double-strand oligonucleotide of a particular base sequence (e.g., DNA encoding ZPT2-5, ZPT3-1 or ZPT4-1 derived from *Petunia*) and another base sequence having a high level of homology with the particular base sequence (e.g., DNA encoding a homolog of ZPT2-5, ZPT3-1 or ZPT4-1 which is present in a plant other than *Petunia*). A representative example of the stringent conditions applied to the present invention are the following: hybridization is conducted in a solution containing 1M NaCl, 1% SDS, 10% dextran sulfate, $^{32}$P-labeled probe DNA ($1\times10^7$ cpm) and 50 μg/ml salmon sperm DNA at 60° C. for 16 hours, followed by washing twice with 2×SSC/1% SDS at 60° C. for 30 minutes.

In the present invention, a degenerate primer pair corresponding to a conserved region of an amino acid sequence encoded by the gene of a known transcription factor may be used in order to isolate DNAs encoding ZPT2-5, ZPT3-1 and ZPT4-1, and DNA encoding a transcription factor which hybridizes these DNAs under stringent conditions to inhibit the development of pollen. PCR is conducted using this primer pair with cDNA or genomic DNA of a plant as a template, thereafter, the resultant amplified DNA fragment is used as a probe so that the cDNA or genomic library of the same plant can be screened. As an example of such a primer pair, a combination of 5'-CARGCNYTNGGNGGNCAY-3' (SEQ ID NO: 9), and 3'-RTGNCCNCCNARNGCYTG-5' (SEQ ID NO: 10) is illustrated (where N indicates inosine, R indicates G or A, and Y indicates C or T). The above-described primer sequences each correspond to an amino acid sequence QALGGH included in the zinc finger motifs of the above-described ZPT transcription factors.

Therefore, the stringent hybridization conditions which are applied to the present invention may also be used for PCR. In a representative example, the above-described degenerate primers (SEQ ID NOs: 9 and 10) may be used. In this case, the PCR reaction conditions may be the following: denaturation at 94° C. for 5 minutes; followed by 30 cycles of 30 seconds at 94° C., 30 seconds at 50° C. and 1 minute at 72° C.; and finally, incubation at 72° C. for 7 minutes.

PCR may be conducted based on the manufacturer's instruction for a commercially available kit and device, or a method well known to those skilled in the art. A method for preparing a gene library, a method for cloning a gene, and the like are also well known to those skilled in the art. For example, see Sambrook et al., Molecular Cloning: A Laboratory Manual, 2nd Ed. (Cold Spring Harbor Laboratory, 1989). The base sequence of a resultant gene may be determined with a nucleotide sequencing analysis method known in the art, or by a commercially available automatic sequencer.

In the present specification, "controlling the development of pollen" by a transcription factor representatively means that when the expression of this transcription factor is inhibited, a significant change in the form or functions of pollen is observed. Representatively, by inhibiting the expression of a gene encoding the transcription factor of the present invention, preferably about 75% or more, more preferably about 90% or more, and even more preferably about 95% or more of pollen cells are killed before being matured. When the amount of mRNA measured by a Northern blot method is about one tenth or less as compared to a wild-type control plant, the expression of a transcription factor is judged to be inhibited.

Whether or not the transcription factors encoded by genes isolated and identified by screening as above (i.e., ZPT2-5, ZPT3-1 and ZPT4-1, and the homologs thereof) control the development of pollen, can be confirmed by producing a transformed plant and observing the characteristics of the pollen of the plant in accordance with the disclosure of the present specification.

According to the present invention, DNA encoding a transcription factor which controls the development of pollen can be utilized to inhibit the expression of an endogenous gene having the same or homologous base sequence as that of the DNA in plant cells. Such a target endogenous gene is also a transcription factor which controls the development of pollen. According to the method of the present invention, plants are conferred male sterility by selectively inhibiting only the expression of an endogenous transcription factor, preferably without substantially inhibiting the expression of genes other than the endogenous transcription factor which controls the development of pollen.

In other words, plant cells to which the expression inhibiting technique of the present invention is applied are plant cells having an endogenous transcription factor which controls the development of pollen. The gene encoding this endogenous transcription factor is defined as a gene which hybridizes with DNA encoding the above-described ZPT2-5, ZPT3-1 or ZPT4-1, or a homolog thereof under stringent conditions. The definition of the "stringent conditions" is the same as that described in relation to specification of the homologs of ZPT2-5, ZPT3-1 and ZPT4-1. Plants capable of being conferred male sterility with the above-described method are preferably plants which are phylogenetically, closely related to *Petunia* from which the above-described ZPT genes are isolated, or plants from which genes encoding the above-described ZPT homologs are isolated, but the present invention is not intended to be limited to this. "Plants which are phylogenetically, closely related" means representatively plants categorized into the same order, preferably categorized into the same family, more preferably categorized into the same genus, and even more preferably categorized into the same species. Considering the fact that the development of pollen is essential for the reproduction of spermatophyte, it could be easily understood that transcription factors having the same or similar function to that of ZPT2-5, ZPT3-1 and ZPT4-1 may be widely present in other plants.

As a technique for suppressing the expression of an endogenous gene, cosuppression and antisense techniques may be utilized, representatively. As to cosuppression, when a recombinant gene is introduced into a plant cell, the expression of both the gene itself and an endogenous gene including a sequence homologous to part of that gene are suppressed. When cosuppression is utilized, an expression cassette according to the present invention includes DNA encoding a transcription factor or a fragment thereof in the form linked in a forward direction with respect to the promoter. After DNA encoding a transcription factor or a fragment thereof is introduced into a plant cell as an expression cassette, the DNA or fragment thereof can be transcribed in the sense direction under control of the promoter. Due to the action of the introduced DNA, it is possible to suppress the targeted gene expression. Cosuppression can be observed in some transformed plant individuals, but mostly, cosuppression does not occur sufficiently in other individuals. Therefore, typically, individuals in which gene expression is suppressed in an intended manner are screened with routine procedures.

Antisense means that when a recombinant gene is introduced into a plant cell, the transcribed product (mRNA) of the introduced gene forms a hybrid with the complementary sequence of the transcribed product (mRNA) of an endogenous gene so that the translation of a protein encoded by the endogenous gene is inhibited. When antisense is utilized, the expression cassette of the present invention includes DNA encoding a transcription factor or a fragment thereof in the form linked in a reverse direction with respect to the promoter. After DNA encoding a transcription factor or a fragment thereof is introduced into a plant cell as an expression cassette, the DNA or fragment thereof may be transcribed in the antisense direction under control of the promoter. Due to the action of the antisense transcripts, it is possible to suppress the expression of the targeted gene.

(Promoters Derived from ZPT3-1 and ZPT4-1 Genes)

A promoter useful in a method for producing a plant having a modified trait according to the fourth and fifth aspects of the invention is a promoter which includes any of (a') DNA having a sequence from position 1 to position 2624 of a base sequence indicated by SEQ ID NO: 7; (a") DNA having a sequence from position 1 to position 3631 of a base sequence indicated by SEQ ID NO: 8; and DNA having a part of the sequences (a') or (a") and which exhibits promoter activity specific to microspores. The above-described promoter of the present invention is preferably the promoter of (a') or (a"), i.e., the promoter for the ZPT3-1 or ZPT4-1 gene.

A sequence having promoter activity specific to microspores, which is obtained by removing a sequence which is not essential for tissue-specific expression activity from the promoter regions for the ZPT3-1 and ZPT4-1 genes, falls within the scope of the present invention. Such a sequence can be obtained by conducting a promoter deletion experiment in accordance with a commonly used method. Briefly, a plasmid obtained by fusing various promoter region deletion mutants of the ZPT3-1 or ZPT4-1 gene (e.g., mutants obtained by deleting the promoter region from the 5' upstream side of the ZPT3-1 or ZPT4-1 gene in various lengths), and an appropriate reporter gene (e.g., the GUS gene) can be used to measure the tissue-specific promoter activity of the deletion mutants, thereby identifying a region essential for the activity.

Once the region essential for the promoter activity is identified, it is possible that a sequence within or adjacent to the region is modified so that the magnitude of the expression activity of the promoter is increased. The thus-obtained variants also fall within the present invention as long as the variants exhibit promoter activity specific to microspores.

In the present invention, "exhibit promoter activity specific to microspores" means that the ability of a promoter to initiate the transcription of DNA to direct gene expression in a naturally-occurring plant or a plant to which the promoter is introduced as an expression cassette in which the promoter is linked to an arbitrary structural gene, is exhibited specifically in microspores. Here, "specific" means that the expression activity of a promoter is higher than in all the other tissues of the flower of the same plant (including tapetum layer, filament, style, capitulum, petal, calyx, and the like; note that the dehiscence tissue of the anther is excluded). The above-described specific promoter preferably has an expression activity in microspores, higher than the expression activity in all the other tissues of the flower and portions other than the flower of the same plant (roots, leaves, stems, and the like). More preferably, the specific promoter exhibits substantially no activity in all the other tissues of the flower and portions other than the flower of the same plant. "Exhibit the promoter activity specific to the dehiscence tissue of the anther" is defined in a manner similar to that described above. The magnitude of expression activity may be evaluated by comparing the expression level of a promoter in microspores with the expression level of the same promoter in other flower tissues in accordance with a commonly used method. The expression level of a promoter is typically determined by the production amount of the products of a gene expressed under control of the promoter.

The above-described method of the present invention utilizing a specific promoter is intended to modify a trait related to reproduction of a plant. "Modify" means that at least a portion of the reproductive organ of a post-transformation plant loses a function which existed in the pre-transformation plant (wild type or horticulture breed), acquires a function which did not exist in the pre-transformation plant, or has an increased or decreased level of particular function as compared to the pre-transformation plant. Such modification of a trait can be achieved as a result of the microspore-specific expression of any heterologous gene operatively linked to the promoter of the present invention under the control of the promoter in a transformed plant into which the gene has been introduced. It is well known that in a number of tissue-specific promoters, the tissue-specificity is conserved among species. Therefore, it is easily understood that the promoter of the present invention can be applied to a wide variety of plant species. The degree of trait modification may be evaluated by comparing the trait of a post-transformation plant with the trait of the pre-transformation plant. As a preferable trait to be modified, female sterility and self-incompatibility are illustrated, but such a trait is not limited to these.

For example, the promoter of the present invention can be obtained by screening the genomic library of a plant using known cDNA as a probe, and isolating an upstream sequence of a coding region from the corresponding genomic clone. As an example of cDNA, cDNA of the above-described transcription factors derived from *Petunia*, ZPT3-1 and ZPT4-1, are illustrated.

The promoter of the present invention is not limited to that isolated from the nature, but may include synthesized polynucleotides. For example, synthesized polynucleotides may be obtained by synthesizing or modifying the sequence of a promoter sequenced as described above or an active region thereof with a method well-known to those skilled in the art.

(Construction of Expression Cassette and Expression Vector)

DNA encoding the transcription factor of the present invention can be introduced into plant cells as an expression cassette, in which the DNA is operatively linked to an appropriate promoter using a method well known to those skilled in the art, with a known gene recombinant technique. Similarly, the microspore-specific promoter of the present invention can be introduced into plant cells as an expression cassette in which the promoter is operatively linked to a desired heterologous gene.

A "promoter" which can be linked to the above-described transcription factor means any promoter which expresses in plants, including any of a constitutive promoter, a tissue-specific promoter, and an inducible promoter.

"Constitutive promoter" refers to a promoter which causes a structural gene to be expressed at a certain level irrespective of stimuli inside or outside plant cells. When a heterologous gene is expressed in other tissues or organs of a plant and a plant is not given an undesired trait, use of a constitutive promoter is simple and preferable. As examples of such a constitutive promoter, 35S promoter (P35S) of cauliflower mosaic virus (CaMV), and the promoter for nopaline synthase (Tnos) are illustrated, but the constitutive promoter is not limited to these.

In the present invention, "tissue-specific promoter" refers to a promoter which causes a structural gene to be expressed specifically in at least microspores. Such a tissue-specific promoter includes the promoters derived from ZPT3-1 and ZPT4-1 genes of the present invention and, in addition, other known promoters having anther-specific expression activity. Therefore, use of an expression cassette of the naturally-occurring ZPT3-1 and ZPT4-1 genes comprising a microspore-specific promoter and a sequence encoding a transcription factor optionally combined with another regulatory element, falls within the present invention.

"Inducible promoter" refers to a promoter which causes a structural gene to be expressed in the presence of a particular stimulus, such as chemical agents, physical stress, and the like, and which does not exhibit expression activity in the absence of the stimulus. As an example of such an inducible promoter, a glutathione S-transferase (GST) promoter which can be induced by auxin (van der Kop, D. A. et al., Plant Mol. Biol., 39:979, 1999) is illustrated, but the inducible promoter is not limited to this.

In the present specification, the term "expression cassette" or "plant expression cassette" refers to a nucleic acid sequence including DNA encoding the transcription factor of the present invention and a plant expression promoter operatively (i.e., in such a manner that can control the expression of the DNA) linked to the DNA, and a nucleic acid sequence including the microspore-specific promoter of the present invention and a heterologous gene operatively (i.e., in-frame) linked to the promoter.

"Heterologous gene" which may be linked to the above-described microspore-specific promoter refers to any of endogenous genes of *Petunia* other than the ZPT3-1 and ZPT4-1 gene, endogenous genes in a plant other than *Petunia*, or genes exogenous to plants (e.g., genes derived from animals, insects, bacteria, and fungi), where the expression of products of such a gene are desired in microspores. A preferable example of such a heterologous gene in the present invention is a gene which encodes a cytotoxic gene product and whose expression inhibits the development of pollen. As a specific example of such a gene, the barnase gene (Beals, T. P. and Goldberg, R. B., Plant Cell, 9:1527, 1997) is illustrated, but the present invention is not limited to this.

"Plant expression vector" refers to a nucleic acid sequence including an expression cassette and, in addition, various regulatory elements linked to the cassette in such a manner that the regulatory elements can be operated in host plant cells. Preferably, such a plant expression vector may include a terminator, a drug-resistant gene, and an enhancer. It is well known matter to those skilled in the art that the types of plant expression vectors and the types of regulatory elements used may be varied depending on host cells. Plant expression vectors used in the present invention may further have a T-DNA region. The T-DNA region increases the efficiency of gene introduction, particularly when *Agrobacterium* is used to transform a plant.

"Terminator" is a sequence which is located downstream of a region encoding a protein of a gene and which is involved in the termination of transcription when DNA is transcribed in to mRNA, and the addition of a poly A sequence. It is known that a terminator contributes to the stability of mRNA, and has an influence on the amount of gene expression. As examples of such a terminator, the terminator for the nopaline synthase gene (Tnos), and the 35S terminator of cauliflower mosaic virus (CaMV) are illustrated, but the terminator is not limited to these.

"Drug-resistant gene" is desirably one that facilitates the selection of transformed plants. The neomycin phosphotransferase II (NPTII) gene for conferring kanamycin resistance, and the hygromycin phosphotransferase gene for conferring hygromycin resistance may be preferably used, but the drug-resistant gene is not limited to these.

The plant expression vector of the present invention may be prepared using a gene recombinant technique well known to those skilled in the art. A plant expression vector is constructed, for example, preferably using pBI-type vectors or pUC-type vectors, but the plant expression vector is not limited to these.

(Production of Transformed Plant)

The thus-constructed expression cassette, or an expression vector including the expression cassette, may be introduced into desired plant cells using a known gene recombinant technique. The introduced expression cassette is present to be integrated into DNA in a plant cell. It should be noted that DNA in a plant cell includes not only chromosome but also DNA included in various organelles included in a plant cell (e.g., a mitochondria, and a chloroplast).

In the present specification, the term "plant" includes any of monocotyledons and dicotyledons. Preferable plants are dicotyledons. Dicotyledons include any of Archichlamiidae and Sympetalidae. A preferable subclass is Sympetalidae. Sympetalidae includes any of Gentianales, Solanales, Lamiales, Callitrichales, Plantaginales, Campanulales, Scrophulariales, Rubiales, Dipsacales, and Asterales. A preferable order is Solanales. Solanales includes any of Solanaceae, Hydrophyllaceae, Polemoniaceae, Cuscutaceae, and Convolvulaceae. A preferable family is Solanaceae. Solanaceae includes *Petunia, Datura, Nicotiana, Solanum, Lycopersicon, Capsicum, Physalis, Lycium*, and the like. Preferable genera are *Petunia, Datura,* and *Nicotiana*, and more preferably *Petunia*. The genus *Petunia* includes the following species: *P. hybrida, P. axillaris, P. inflata, P. violacea*, and the like. A preferable species is *P. hybrida*. "Plant" means phanerogamic plants and seed obtained from the plants unless otherwise specified.

As examples of "plant cells", cells in each tissue of plant organs, such as flowers, leaves, roots, and the like, callus, and suspension cultured cells are illustrated.

For the purpose of introduction of a plant expression vector into a plant cell, a method well known to those skilled in the art, such as an indirect method using *Agrobacterium*, and a method for directly introducing into cells, can be used. As such an indirect method using *Agrobacterium*, for example, a method of Nagel et al. (FEMS Microbiol. Lett., 67:325 (1990)) may be used. In this method, initially, *Agrobacterium* is transformed with a plant expression vector (e.g., by electroporation), and then the transformed *Agrobacterium* is introduced into a plant cell with a well-known method, such as a leaf disk method and the like. As a method for directly introducing a plant expression vector into a cell, an electroporation method, particle gun, a calcium phosphate method, a polyethylene glycol method, and the like are illustrated. These methods are well known in the art. A method suitable for a plant to be transformed can be appropriately selected by those skilled in the art.

Cells into which a plant expression vector has been introduced are screened for drug resistance, such as kanamycin resistance and the like, for example. A selected cell may be regenerated to a plant using a commonly used method.

Whether or not an introduced plant expression vector is operative in a regenerated plant can be confirmed with a technique well-known to those skilled in the art. For example, in the case where suppression of the expression of an endogenous gene is intended, such confirmation can be conducted by measuring the level of transcription with Northern blot analysis. In this manner, a desired transformed plant in which the expression of an endogenous transcription factor is suppressed can be selected. For the purpose of the expression of a heterologous gene using a tissue-specific promoter, the expression of the heterologous gene can be confirmed usually by Northern blot analysis using RNA extracted from a target tissue as a sample. The procedures of this analysis method are well known to those skilled in the art.

Whether or not the expression of an endogenous transcription factor is suppressed in accordance with the method of the present invention so that pollen fertility is reduced can be confirmed, for example, by observing the form of the pollen of a plant, which is transformed by an expression vector including DNA encoding a transcription factor, with a microscope optionally after histochemically staining.

Whether or not a promoter is expressed specifically in a microspore in accordance with the method of the present invention can be confirmed by, for example, histochemically staining flower tissues including the anther in a plant transformed with an expression vector, in which a promoter is operatively linked to the GUS gene, by a commonly used method to detect the distribution of GUS activity.

EXAMPLES

Hereinafter, the present invention will be described based on examples. The scope of the present invention is not limited to the examples only. Restriction enzymes, plasmids, and the like used in the examples are available from commercial sources.

Example 1

Construction of Plant Expression Vector Including Polynucleotide Encoding ZPT Transcription Factors Out of the previously reported anther-specific ZF genes (Kobayashi et al., above), cDNAs of PEThy ZPT2-5 (ZPT2-5), PEThy ZPT3-1 (ZPT3-1), and PEThy ZPT4-1 (ZPT4-1) were each linked downstream of the 35S promoter of the cauliflower mosaic virus to prepare a plant expression vector. This preparation will be specifically described below.

Example 1-1

DNA fragments including the cauliflower mosaic virus 35S promoter (HindIII-XbaI fragment) and DNA fragments including the NOS terminator (SacI-EcoRI fragment) in plasmid pBI221 (purchased from CLONTECH Laboratories Inc.) were successively inserted into the multi-cloning site of plasmid pUCAP (van Engelen, F. A. et al., Transgenic Res., 4:288, 1995) to prepare pUCAP35S. A pBluescript vector including cDNA of ZPT2-5 was cleaved at KpnI and SacI sites (either is a site within the vector), and inserted between KpnI and SacI sites of the above-described pUCAP35S. Further, this recombinant plasmid was cleaved with EcoRI and HindIII, and a DNA fragment encoding ZPT2-5 was inserted between EcoRI and HindIII sites of binary vector pBINPLUS (van Engelen, F. A. et al., above). As shown in FIG. 4(a), the constructed ZPT2-5 gene comprises the 35S promoter region (P35S; 0.9 kb) of cauliflower mosaic virus (CaMV), a polynucleotide (ZPT2-5; about 0.8 kb) encoding ZPT2-5 of the present invention, and the terminator region of nopaline synthase (Tnos; 0.3 kb). Pnos in FIG. 4 indicates the promoter region of nopaline synthase, and NPTII indicates the neomycin phosphotransferase II gene.

Example 1-2

A pBluescript vector including cDNA of ZPT3-1 was cleaved at KpnI site and SacI site (either is a site within the vector), and inserted between KpnI and SacI sites of pUCAP35S. Further, this recombinant plasmid was cleaved with EcoRI and HindIII, and a DNA fragment encoding ZPT3-1 was introduced between EcoRI and HindIII sites of binary vector pBINPLUS. As is apparent from FIG. 4(b), the constructed ZPT3-1 gene comprises the 35S promoter region (P35S; 0.9 kb) of cauliflower mosaic virus (CaMV), a polynucleotide (ZPT3-1; about 1.7 kb) encoding ZPT3-1 of the present invention, and the terminator region (Tnos; 0.3 kb) of nopaline synthase.

Example 1-3

A pBluescript vector including cDNA of ZPT4-1 was cleaved at KpnI site and SacI site (either is a site within the vector), and inserted between KpnI and SacI sites of the above-described pUCAP35S. Further, this recombinant plasmid was cleaved with EcoRI and HindIII, and a DNA fragment encoding ZPT4-1 was introduced between EcoRI and HindIII sites of binary vector pBINPLUS. As is apparent from FIG. 4(c), the constructed ZPT4-1 gene comprises the 35S promoter region (P35S; 0.9 kb) of cauliflower mosaic virus (CaMV), a polynucleotide (ZPT4-1; about 2.0 kb) encoding ZPT4-1 of the present invention, and the terminator region (Tnos; 0.3 kb) of nopaline synthase.

Example 2

Isolation of ZPT3-1 and ZPT4-1 Promoter Regions and Linkage to GUS Reporter Gene cDNAs of ZPT3-1 and ZPT4-1 were used as probes to isolate corresponding genomic clones from the genome DNA library of *Petunia*. DNA fragments (promoter region; about 2.7 kb and about 3.6 kb) upstream of the transcription initiation site were subcloned. Each DNA fragment was linked upstream of the GUS reporter gene and cloned into a binary vector. This preparation will be specifically described below.

Example 2-1 cDNA of ZPT3-1 was labeled with [$\alpha$-$^{32}$P]dCTP using a commonly used random priming method (Sambrook et al., above) to prepare a radiolabeled probe. With this probe, a genomic library of *Petunia* (*Petunia hybrida* var. *Mitchell*) prepared within EMBL3 vector (manufactured by Stratagene) was screened. A genome DNA fragment (PstI-SacI) of about 2.7 kb including the upstream region of the gene from the resultant clone was subcloned at PstI-SacI site of pBluescriptSK vector (pBS-ZPT3-1-PS), followed by sequencing (FIG. 5). Next, this plasmid was used as a template to conduct PCR using a primer including a SalI recognition sequence (3'-TATGGAGCTCGTCGACAG TTGATGGTTCATTTTTCTGGCTATTGTC-5'; SEQ ID NO: 11) and a commercially available M13–20 primer, so that SalI site was introduced immediately downstream of the initiation site of translation of the ZPT3-1 protein (base position: 2661). Thereafter, a DNA fragment cleaved with PstI and SalI was inserted upstream of the GUS coding region of pUCAPGUSNT (pUCAP-ZPT3-1-GUSNT). Therefore, the ZPT3-1 gene was connected to the GUS coding region in frame at a region near the N terminus of the coding region of the ZPT3-1 gene. Further, a DNA fragment obtained by cleaving pUCAP-ZPT3-1-GUSNT with AscI and PacI (including the ZPT3-1 promoter, the GUS coding region and the NOS terminator) was inserted into pBIN-PLUS vector to obtain pBIN-ZPT3-1-GUS (FIG. 7(a)).

Example 2-2

As to ZPT4-1, similarly, genomic DNA was isolated, and a DNA fragment (EcoRI—EcoRI) of about 3.6 kb including an upstream region of the ZPT4-1 gene was subcloned at the EcoRI—EcoRI site of pBluescriptSK vector (pBS-ZPT4-1-EE), followed by sequencing (FIG. 6). This plasmid was used as a template to conduct PCR using a primer including a BamHI recognition sequence (3'-CATGGATATAGGATC-CTATATC-5'; SEQ ID NO: 12) and M13–20 primer, so that BamHI site was introduced immediately downstream of the initiation site of translation of the ZPT4-1 protein (base position: 3641). Thereafter, a DNA fragment cleaved with EcoRI and BamHI was inserted upstream of the GUS coding region of pUCAPGUSNT (pUCAP-ZPT4-1-GUSNT). Therefore, the ZPT4-1 gene was connected to the GUS coding region in frame at a region near the N terminus of the coding region of the ZPT4-1 gene. Further, a DNA fragment (AscI-PacI) was inserted into pBINPLUS vector to obtain pBIN-ZPT4-1-GUS in a manner similar to that described above (FIG. 7(b)).

Example 3

Introduction of Each Fusion Gene into Petunia Cells

Each of the above-described expression vectors was introduced via Agrobacterium into Petunia (Petunia hybrida var. Mitchell) with the following procedures.

(1) Agrobacterium tumefaciens LBA4404 strain (purchased from CLONTECH Laboratories Inc.) was cultured at 28° C. in L medium containing 250 mg/ml of streptomycin and 50 mg/ml of rifampicin. Cell suspension was prepared in accordance with the method of Nagel et al. (1990) (above). The plasmid vector constructed in Examples 1 and 2 were introduced into the above-described strain by electroporation.

(2) A polynucleotide encoding each fusion gene was introduced into Petunia cells using the following method: the Agrobacterium tumefaciens LBA4404 strain obtained in the above-described (1) was shake-cultured (28° C., 200 rpm) in YEB medium (DNA Cloning, Vol. 2, page 78, Glover D. M. Ed., IRL Press, 1985). The resultant culture was diluted with sterilized water by a factor of 20, and cocultured with leaf pieces of Petunia (Petunia hybrida var. Mitchell). After 2 to 3 days, the above-described bacterium was removed in medium containing antibiotics. The Petunia cells were subcultured with selection medium every two weeks. The transformed Petunia cells were selected based on the presence or absence of kanamycin resistance due to the expression of the NPTII gene derived from pBINPLUS which had been introduced along with the above-described five fusion genes. The selected cells were induced into callus with a commonly used method. The callus was redifferentiated into a plant (Jorgensen R. A. et al., Plant Mol. Biol., 31:957, 1996).

Example 4

Phenotype of Transformed Petunia into which ZPT Genes are Introduced

The transformants obtained by introducing the vector of Example 1 were used to observe change in the form of pollen in association with the control of the expression of ZPT2-5, ZPT3-1 and ZPT4-1, so that the influence of the introduced cDNA of these ZPT genes on plants were studied. This study will be described below in detail.

Example 4-1

From transformants (14 individuals) into which cDNA of ZPT2-5 had been introduced under the control of a 35S promoter, individuals (3 individuals) in which gene expression was suppressed by cosuppression were selected by Northern blot analysis (note that over expression of the ZPT2-5 gene introduced was observed in four individuals out of the 14 individuals). The conditions of the Northern blot analysis were the following: hybridization was conducted in a solution containing 7% SDS, 50% formamide, 5×SSC, 2% blocking reagent (manufactured by Boehringer Mannheim), 50 mM sodium phosphate buffer (pH 7.0), 0.1% sodium lauryl sarcosine, 50 μg/ml of yeast tRNA, and $^{32}$P-labeled probe DNA ($1\times10^7$ cpm) at 68° C. for 16 hours, followed by washing with 2×SSC/0.1% SDS at 68° C. for 30 minutes.

In the above-described three cosuppression transformants, the following phenotypes were observed (FIG. 8).

In the meiosis process which occurs immediately before the tetrad stage, in the case of normal (wild type) Petunia, chromatin is condensed into thin thread-like structures (prophase I: leptotene), and synapsis of homologous chromosomes occurs (prophase I: zygotene). Thereafter, in metaphase I, chromosome tetrad align along the equatorial plane of the cells, and thereafter the homologous chromosomes are equally separated to the opposite poles of the cells by the spindle apparatus. In the transformant having cosuppression of the ZPT2-5 gene, the separation of the chromosomes to the poles proceeded while chromosome tetrad did not align along the equatorial plane in metaphase I. The division of the chromosomes to the poles was significantly unbalanced.

In the normal process of meiosis, after the above-described first separation of the chromosomes, second separation of the chromosomes forms four haploid groups. Thereafter, separation of cytoplasm occurs. In the case of the above-described transformant having cosuppression, separation of cytoplasm and cell division occurred immediately after the first separation of chromosomes. This unbalanced cell division occurred not only at a single time but also further repeated at least two times, so that 8 microspore cells were formed at the most. Due to the unbalanced separation of chromosomes, the number of chromosomes included in the microspore cells was unequal and, in addition, the size of the cells was significantly unequal. As a result, during the stage corresponding to the tetrad stage of normal Petunia, a more number of microspores (8 or less) than normal were formed in these transformants (FIG. 8(f); a photograph of pollen cells of the ZPT2-5 cosuppression transformant in the bud having a size of 6 mm. Further, FIG. 9(b); see a photograph of pollen cells of the transformant in the tetrad stage).

In the cosuppression transformants, a part of the microspores (10–20%) still continued to develop, but most microspore cells burst before a callose layer enveloping the microspore was degraded. In this stage, the microspores which did not burst and survived were in the abnormal form of substantially a hexahedron, which was clearly different from the tetrahedron form of normal microspores. Thereafter, the abnormal-form microspores became binuclear due to seemingly normal mitosis to form pollen grains. However, most of these pollen grains lost fertility. Specifically, when the pollen grains of these transformants were placed on the pistil of normal Petunia, no or few seeds were formed from pollen of the three strains exhibiting cosuppression (10% or less, i.e., the number of seeds produced by one Petunia is 10% of control as the average of about 10 flowers). For pollen from three transformant strains without cosuppression, normal seed formation was confirmed similar to wild type control plants.

The above-described cosuppression transformant also exhibited abnormality in formation of female gametophyte, and female fertility was reduced to 25–35% of that of normal individuals. Specifically, the development of an ovule (female gametophyte) was seemingly normal, but when wild type pollen was used for pollination, the majority of ovules could not be fertilized and even fertilized ovules exhibited abnormality in the subsequent developement, so that most ovules aborted. In this case, the transformants without cosuppression formed normal female gametophytes similar to wild type control plants.

Figure 9:
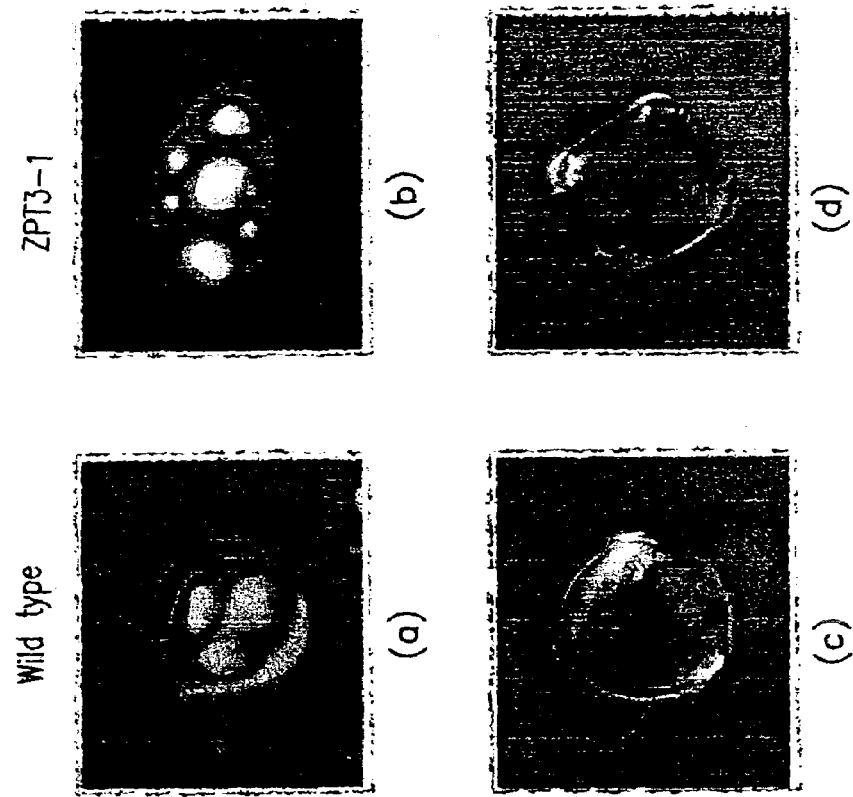
FIG. 9 shows photographs indicating the forms of organisms, i.e., the pollen of a wild type *Petunia* and the pollen of a *Petunia* into which pBIN-35S-ZPT3-1 was introduced (the magnification is 700 times).

Example 4-2 cDNA of ZPT3-1 was introduced under the control of the 35S promoter. As a result, a trait change similar to when the ZPT2-5 gene was introduced appeared in three individuals out of 15 individuals (FIG. 9). Specifically, in these transformants, substantially the same abnormality as that of ZPT2-5 were observed in the process of meiosis. The number of cells which developed up to the microspore stage was very small, and surviving microspores exhibited morphological abnormality (hexahedron). Further, matured pollen grains lost fertility. However, unlike ZPT2-5, the female fertility of these individuals was not affected.

Gene expression was analyzed with the Northern blot method under the same conditions as those in Example 4-1. As a result, in individuals into which the ZPT3-1 gene was introduced, gene expression was suppressed both for ZPT3-1 and ZPT4-1. Both genes share a high level of structural similarity. Specifically, the homology of the base sequence in the entire coding region is 37%. When the second ZF region of ZPT3-1 and the third ZF region of ZPT4-1, and the third ZF region of ZPT3-1 and the fourth ZF region of ZPT4-1, including neighboring sequences, are respectively compared with each other at the base sequence level in such a manner that the homology value is maximized, the average of the homology is 86% (the comparison of the sequences was conducted using the Clustal V program). Therefore, it is highly likely that the above-described expression suppressing phenomenon is caused by the introduction of one gene leading to the suppression of the expression of two genes (cosuppression). This suggests that the functions of these two genes overlap, and is consistent in that by the introduction of either gene, a common change in a phenotype could be observed.

Example 4-3 cDNA of ZPT4-1 was introduced under the control of the 35S promoter. As a result, a trait change similar to when the ZPT2-5 gene was introduced appeared in two individuals out of 13 individuals. Specifically, in these transformants, substantially the same abnormality as that of ZPT2-5 were observed in the process of meiosis. The number of cells which developed up to the microspore stage was very small, and surviving microspores exhibited morphological abnormality (hexahedron). Further, most matured pollen grains lost fertility. However, similar to ZPT3-1, the female fertility of these individuals was not affected. For the above-described reasons, in this example, it is also highly likely that gene expression was suppressed for both ZPT3-1 and ZPT4-1 (cosuppression).

As described above, by introducing a gene encoding ZPT2-5, ZPT3-1 or ZPT4-1, the development of pollen can be inhibited and the fertility can be eliminated with excellent efficiency (99% or more for ZPT3-1, and 90% or more for ZPT2-5 and ZPT4-1). The introduction of these genes may be useful for a selective trait transformation technique since the effects of the genes are specific to pollen (pollen and female gametophyte in the case of ZPT2-5) and the other traits of plants are not affected.

Example 5

Tissue Specificity of Promoter Activity of ZPT3-1 and ZPT4-1

The tissue-specific promoter activity of the above-described DNA fragments was detected by histochemical staining with GUS activity using the transformants obtained by introducing the vector in Example 2. This will be described below in detail.

Example 5-1

Figure 10:
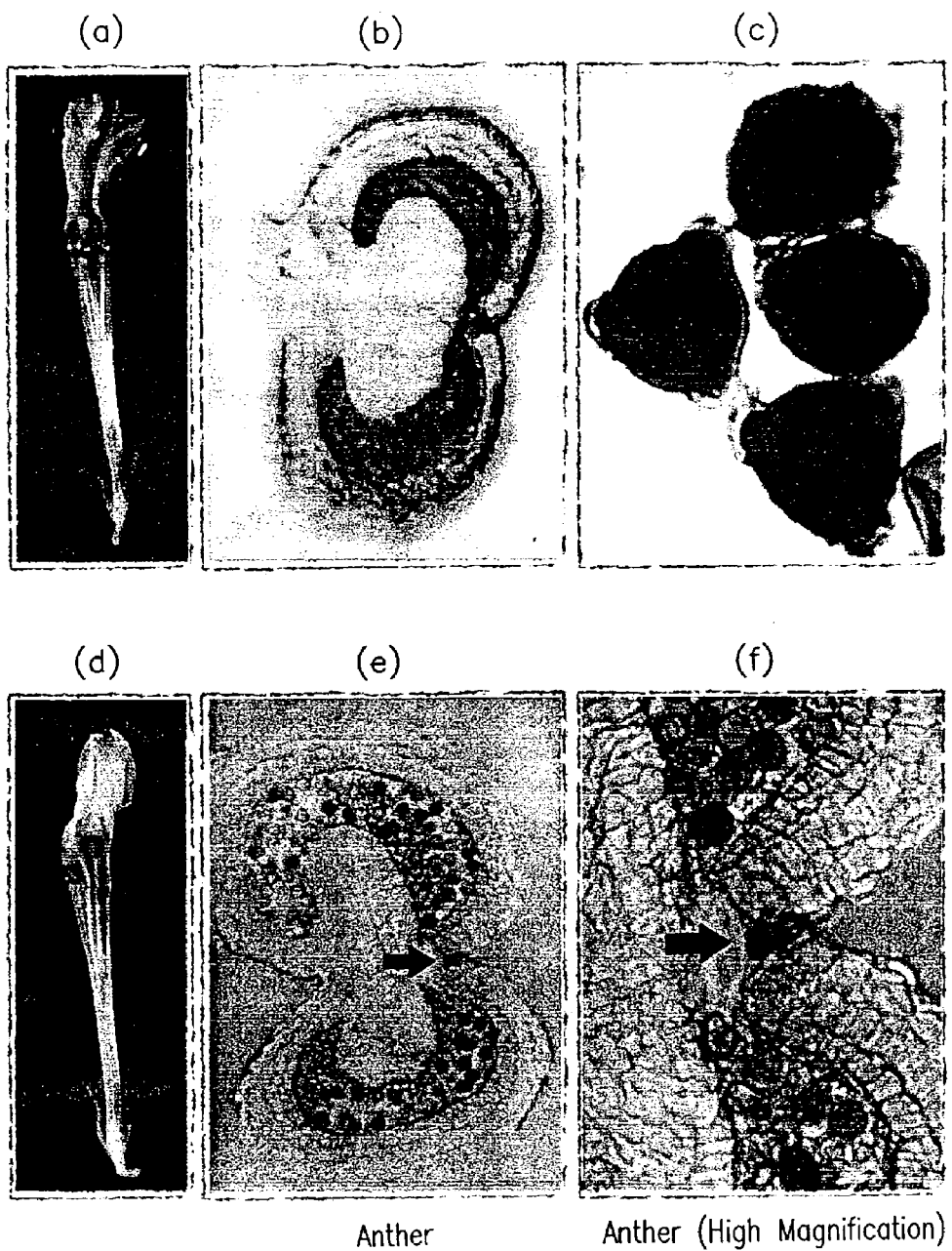
FIG. 10 shows photographs showing the forms of organisms, i.e., GUS-stained floral organs of *Petunia* into which pBIN-ZPT3-1-GUS and pBIN-ZPT4-1-GUS were introduced. Each photograph was taken of a flower (bud) whose anther is in the uninucleate stage.

The flowers of the transformants obtained by introducing a fusion gene of the upstream region of the ZPT3-1 gene with GUS were used to study the distribution of GUS activity using X-GUS as a substrate (Gallagher, S. R. Ed., GUS protocols: using the GUS gene as a reporter of gene expression, Academic Press, Inc., pp. 103–114, 1992). As a result, GUS activity was detected specifically in microspores in the uninucleate stage (FIGS. 10(a) through (c)).

Example 5-2

The flowers of the transformants obtained by introducing a fusion gene of the upstream region of the ZPT4-1 gene with GUS were used to study the distribution of GUS activity in a manner similar to that described above. As a result, GUS activity was observed specifically in microspores and the dehiscence tissue of anthers from the uninucleate stage to the binucleate stage (FIG. 10(d) through (f); the dehiscence tissue of anthers was indicated by an arrow in FIGS. 10(e) and (f)).

As described above, the promoters for the ZPT3-1 and ZPT4-1 genes exhibit activity specifically in microspores in the uninucleate stage (ZPT3-1) and microspores from the uninucleate stage to the binucleate stage (ZPT4-1), respectively. The promoter for the ZPT4-1 gene also exhibits activity specifically in the dehiscence tissue of anthers from the uninucleate stage to the binucleate stage.

Microspores are precursor cells which will be subsequently matured to form pollen grains. Therefore, these promoters are useful as a tool for detailed research on the development of pollen. Further, these promoters or active fragments thereof can be used to cause a cytotoxic gene or the like to be expressed specifically in microspores to abort pollen cells or eliminate the functions thereof, whereby the development of pollen can be directly and efficiently controlled.

INDUSTRIAL APPLICABILITY

The method of the present invention utilizing DNA encoding transcription factors derived from the ZPT2-5, ZPT3-1 and ZPT4-1 genes, and promoters derived from the ZPT3-1 and ZPT4-1 genes is useful as a technique for selectively modifying the trait of a plant using a genetic engineering method, particularly a technique for conferring male sterility.

What is claimed is:

1. A method for producing a male sterile plant of the genus *Petunia*, comprising the steps of:

providing a plant expression cassette comprising a nucleic acid consisting of a DNA which encodes a zinc finger transcription factor, wherein the DNA has the base sequence from position 1 to position 777 of the base sequence indicated by SEQ ID NO:1 providing *Petunia* plant cells having an endogenous transcription factor controlling the development of pollen, wherein the gene encoding the endogenous transcription factor hybridizes under stringent conditions to the nucleic acid;

introducing the expression cassette into the plant cells;

regenerating the plant cells, into which the expression cassette has been introduced, into plants to produce regenerated plants, and screening the regenerated plants for one in which the nucleic acid is expressed so that expression of the endogenous transcription factor is suppressed.

2. The method according to claim 1, wherein the nucleic acid is linked in a forward direction with respect to the promoter, and is transcribed in the sense direction in cells of the plant.

3. The method according to claim 1, wherein the nucleic acid is linked in a reverse direction with respect to the promoter, and is transcribed in an antisense direction in cells of the plant.

4. The method according to claim 1, wherein the expression cassette is incorporated into a plant expression vector.

5. A male sterile plant produced by the method according to any one of claim 2, 3 or 4.

* * * * *

SEQUENCE LISTING

```
<160> NUMBER OF SEQ ID NOS: 14

<210> SEQ ID NO 1
<211> LENGTH: 777
<212> TYPE: DNA
<213> ORGANISM: Petunia hybrida
<220> FEATURE:
<221> NAME/KEY: CDS
<222> LOCATION: (58)..(588)

<400> SEQUENCE: 1
atcaaaacca aaattccttt ttcacaccga agaacagcct tagtatttca agaaaac          57 atg gtg gct cta tca acg aag aga gaa aga gaa gaa gat aac ttt tac       105
Met Val Ala Leu Ser Thr Lys Arg Glu Arg Glu Glu Asp Asn Phe Tyr
  1               5                  10                  15 agc ata aca acc atg gca aat tac ttg atg tta ctc tcg cgc caa gca       153
Ser Ile Thr Thr Met Ala Asn Tyr Leu Met Leu Leu Ser Arg Gln Ala
             20                  25                  30 aat gaa cat ttt gac aag aaa atg aac aac tca agt act agt cga gtt       201
Asn Glu His Phe Asp Lys Lys Met Asn Asn Ser Ser Thr Ser Arg Val
         35                  40                  45 ttc gag tgc aag act tgt aat cgc cag ttt tca tct ttt caa gca cta       249
Phe Glu Cys Lys Thr Cys Asn Arg Gln Phe Ser Ser Phe Gln Ala Leu
     50                  55                  60 ggt ggc cat aga gca agt cac aag aag cca aga tta atg gga gaa ttg       297
Gly Gly His Arg Ala Ser His Lys Lys Pro Arg Leu Met Gly Glu Leu
 65                  70                  75                  80 cat aac ttg caa tta ttt cat gaa ttg cct aaa cgt aaa act cac gag       345
His Asn Leu Gln Leu Phe His Glu Leu Pro Lys Arg Lys Thr His Glu
                 85                  90                  95 tgc tcc att tgt ggg ctt gag ttc gcc att ggg caa gct tta gga gga       393
Cys Ser Ile Cys Gly Leu Glu Phe Ala Ile Gly Gln Ala Leu Gly Gly
            100                 105                 110 cat atg aga agg cat aga gct gtg ata aat gat aaa aat ctt caa gct       441
His Met Arg Arg His Arg Ala Val Ile Asn Asp Lys Asn Leu Gln Ala
        115                 120                 125 cct gat gat caa cat gct cct gtc gtc aaa aaa gca aat ggt cgg aga       489
Pro Asp Asp Gln His Ala Pro Val Val Lys Lys Ala Asn Gly Arg Arg
    130                 135                 140 att ttg tcc ttg gat ttg aac ttg acg cca ttg gaa aat gac tta gag       537
Ile Leu Ser Leu Asp Leu Asn Leu Thr Pro Leu Glu Asn Asp Leu Glu
145                 150                 155                 160 ttt gat ttg cga aag agt aat act gct cct atg gtc gat tgc ttt tta       585
Phe Asp Leu Arg Lys Ser Asn Thr Ala Pro Met Val Asp Cys Phe Leu
                165                 170                 175 tga ttgaactttc cgtttcctta ttctttttctc ttcttctttt ggatattgta           638
tttattcatt aattgtagga gggataggaa gtcttatctt gtgtattagt actacatttt      698
gcagattgta gaacgattag tttgtaactt atcatgatac ccgaaataca atactattta      758
```

```
                                                              -continued
tatgattatt atactacac                                                777
```

<210> SEQ ID NO 2
<211> LENGTH: 176
<212> TYPE: PRT
<213> ORGANISM: Petunia hybrida

<400> SEQUENCE: 2

```
Met Val Ala Leu Ser Thr Lys Arg Glu Arg Glu Glu Asp Asn Phe Tyr
 1               5                  10                  15

Ser Ile Thr Thr Met Ala Asn Tyr Leu Met Leu Leu Ser Arg Gln Ala
                20                  25                  30

Asn Glu His Phe Asp Lys Lys Met Asn Asn Ser Ser Thr Ser Arg Val
            35                  40                  45

Phe Glu Cys Lys Thr Cys Asn Arg Gln Phe Ser Ser Phe Gln Ala Leu
        50                  55                  60

Gly Gly His Arg Ala Ser His Lys Lys Pro Arg Leu Met Gly Glu Leu
 65                  70                  75                  80

His Asn Leu Gln Leu Phe His Glu Leu Pro Lys Arg Lys Thr His Glu
                85                  90                  95

Cys Ser Ile Cys Gly Leu Glu Phe Ala Ile Gly Gln Ala Leu Gly Gly
                100                 105                110

His Met Arg Arg His Arg Ala Val Ile Asn Asp Lys Asn Leu Gln Ala
            115                 120                 125

Pro Asp Asp Gln His Ala Pro Val Val Lys Lys Ala Asn Gly Arg Arg
        130                 135                 140

Ile Leu Ser Leu Asp Leu Asn Leu Thr Pro Leu Glu Asn Asp Leu Glu
145                 150                 155                 160

Phe Asp Leu Arg Lys Ser Asn Thr Ala Pro Met Val Asp Cys Phe Leu
                165                 170                 175
```

<210> SEQ ID NO 3
<211> LENGTH: 1640
<212> TYPE: DNA
<213> ORGANISM: Petunia hybrida
<220> FEATURE:
<221> NAME/KEY: CDS
<222> LOCATION: (95)..(1408)

<400> SEQUENCE: 3

```
accggtccgg aattcccggg tcgacccacg cgtccggaaa ctttccttgt tgcactttaa      60
tttatgttct agtgagtata ttagagagtg agaa atg gtg gac aat agc cag aaa     115
                                    Met Val Asp Asn Ser Gln Lys
                                      1               5 aat gaa cca tca act gtt ata cac tat tgt aga gta tgt aaa agg gga      163
Asn Glu Pro Ser Thr Val Ile His Tyr Cys Arg Val Cys Lys Arg Gly
            10                  15                  20 ttt aat agt gct gga gct ctt ggt ggg cac atg aga tct cat gga gtg      211
Phe Asn Ser Ala Gly Ala Leu Gly Gly His Met Arg Ser His Gly Val
        25                  30                  35 gga gat cat aat aaa aac tat ggt gaa gat att aat gaa caa aga tat      259
Gly Asp His Asn Lys Asn Tyr Gly Glu Asp Ile Asn Glu Gln Arg Tyr
 40                  45                  50                  55 atg atc aac aac ttt aga aga gat aaa cca gag ggt caa aag cac tca      307
Met Ile Asn Asn Phe Arg Arg Asp Lys Pro Glu Gly Gln Lys His Ser
                60                  65                  70 tat aat ctt cgt gct aat act aat aga tta tta ggc aat cga gca agt      355
Tyr Asn Leu Arg Ala Asn Thr Asn Arg Leu Leu Gly Asn Arg Ala Ser
            75                  80                  85
```

-continued

```
gaa gat cgt gac aag aag tcc tcg atg tgg cct ccc aat gat cgt ggg      403
Glu Asp Arg Asp Lys Lys Ser Ser Met Trp Pro Pro Asn Asp Arg Gly
         90                  95                 100 aaa tat gcc cta gac gag act cta acc cta tca tca atg tcg tca cca      451
Lys Tyr Ala Leu Asp Glu Thr Leu Thr Leu Ser Ser Met Ser Ser Pro
    105                 110                 115 gga tca tca gat ctt gaa aga agt act aag cca tat gat gca aaa gaa      499
Gly Ser Ser Asp Leu Glu Arg Ser Thr Lys Pro Tyr Asp Ala Lys Glu
120                 125                 130                 135 gtg tat aat gga aat gat aag gac aaa tac gct tca aga gaa gaa gaa      547
Val Tyr Asn Gly Asn Asp Lys Asp Lys Tyr Ala Ser Arg Glu Glu Glu
                140                 145                 150 gaa gat cta gcg aat tgt ttg gtc atg ttg tcg aac aaa tct tat gtt      595
Glu Asp Leu Ala Asn Cys Leu Val Met Leu Ser Asn Lys Ser Tyr Val
            155                 160                 165 ttg tcc gat aac aat gag gca aca tac aag gct gaa gaa gtg gaa aag      643
Leu Ser Asp Asn Asn Glu Ala Thr Tyr Lys Ala Glu Glu Val Glu Lys
        170                 175                 180 ggc atg ttc caa tgt aaa gca tgc aag aaa gtt ttt agc tcc cac caa      691
Gly Met Phe Gln Cys Lys Ala Cys Lys Lys Val Phe Ser Ser His Gln
    185                 190                 195 gct tta ggg gga cat aga gcg agt cat aag aaa gtt aaa ggg tgt tat      739
Ala Leu Gly Gly His Arg Ala Ser His Lys Lys Val Lys Gly Cys Tyr
200                 205                 210                 215 gct gcc aag ata aaa gat gac aac gac ggc aac aac gac aac aac gac      787
Ala Ala Lys Ile Lys Asp Asp Asn Asp Gly Asn Asn Asp Asn Asn Asp
                220                 225                 230 aac aac aat aat gat aat gac atc gat gaa gac tcg atc tct cct agt      835
Asn Asn Asn Asn Asp Asn Asp Ile Asp Glu Asp Ser Ile Ser Pro Ser
            235                 240                 245 gat tta att ttc cat caa gaa tct aac tcg ttt cag tct caa tct cca      883
Asp Leu Ile Phe His Gln Glu Ser Asn Ser Phe Gln Ser Gln Ser Pro
        250                 255                 260 tca tca tcg agc tcg ttt tca agg aag aga tca agg gtt cat caa tgc      931
Ser Ser Ser Ser Ser Phe Ser Arg Lys Arg Ser Arg Val His Gln Cys
    265                 270                 275 tcg att tgt cat cga gtt ttt tca tca gga caa gcc ttg ggt ggg cac      979
Ser Ile Cys His Arg Val Phe Ser Ser Gly Gln Ala Leu Gly Gly His
280                 285                 290                 295 aaa agg tgt cac tgg cta tca tca agt ttg cca gag aat act ttt ata     1027
Lys Arg Cys His Trp Leu Ser Ser Ser Leu Pro Glu Asn Thr Phe Ile
                300                 305                 310 cca act ttt caa gaa atc caa tac cac acc caa gaa caa gga tta ttc     1075
Pro Thr Phe Gln Glu Ile Gln Tyr His Thr Gln Glu Gln Gly Leu Phe
            315                 320                 325 aac aag cca atg ttt acc aac ttt gat caa cca tta gat cta aac ttc     1123
Asn Lys Pro Met Phe Thr Asn Phe Asp Gln Pro Leu Asp Leu Asn Phe
        330                 335                 340 cca gca caa cta ggc aat cca gct gaa ttt gag ttg aaa cta cac aat     1171
Pro Ala Gln Leu Gly Asn Pro Ala Glu Phe Glu Leu Lys Leu His Asn
    345                 350                 355 cca ttt gaa cat gaa ggc cca aga agc tat ctc cag cta tgg aca gac     1219
Pro Phe Glu His Glu Gly Pro Arg Ser Tyr Leu Gln Leu Trp Thr Asp
360                 365                 370                 375 caa caa atc aat act aat tta cat caa aat gag aag tgc aaa gat tca     1267
Gln Gln Ile Asn Thr Asn Leu His Gln Asn Glu Lys Cys Lys Asp Ser
                380                 385                 390 acg gag gat ttg aga agg gaa gaa aat tac aag gac aag gaa gca aaa     1315
Thr Glu Asp Leu Arg Arg Glu Glu Asn Tyr Lys Asp Lys Glu Ala Lys
```

```
                395                 400                 405
ttg agt aac ctt aaa gat gtg aac ttg gat gga ggc tct tct tgg tta   1363
Leu Ser Asn Leu Lys Asp Val Asn Leu Asp Gly Gly Ser Ser Trp Leu
        410                 415                 420 caa gta ggg att ggt cca acc cca gat ata gta gca act ctg taa       1408
Gln Val Gly Ile Gly Pro Thr Pro Asp Ile Val Ala Thr Leu
425                 430                 435 ggttagtaac acagtgatcg ttatgtcagc tacaagtata gtaatatata taccaatgtc 1468 ccaacttata cataaactgt ttaacatatt tatactttcg tattattgtt gtatcgaact 1528 ttcactagtt acaatttgtg attcgtccaa tccctaatat agtagcaaca gacctgtaag 1588 attagtatta tgcgattgtt ttgtcattct acaaaataaa atcgtataat at         1640

<210> SEQ ID NO 4
<211> LENGTH: 437
<212> TYPE: PRT
<213> ORGANISM: Petunia hybrida

<400> SEQUENCE: 4

Met Val Asp Asn Ser Gln Lys Asn Glu Pro Ser Thr Val Ile His Tyr
1               5                   10                  15

Cys Arg Val Cys Lys Arg Gly Phe Asn Ser Ala Gly Ala Leu Gly Gly
            20                  25                  30

His Met Arg Ser His Gly Val Gly Asp His Asn Lys Asn Tyr Gly Glu
        35                  40                  45

Asp Ile Asn Glu Gln Arg Tyr Met Ile Asn Asn Phe Arg Arg Asp Lys
    50                  55                  60

Pro Glu Gly Gln Lys His Ser Tyr Asn Leu Arg Ala Asn Thr Asn Arg
65                  70                  75                  80

Leu Leu Gly Asn Arg Ala Ser Glu Asp Arg Asp Lys Lys Ser Ser Met
                85                  90                  95

Trp Pro Pro Asn Asp Arg Gly Lys Tyr Ala Leu Asp Glu Thr Leu Thr
            100                 105                 110

Leu Ser Ser Met Ser Ser Pro Gly Ser Ser Asp Leu Glu Arg Ser Thr
        115                 120                 125

Lys Pro Tyr Asp Ala Lys Glu Val Tyr Asn Gly Asn Asp Lys Asp Lys
    130                 135                 140

Tyr Ala Ser Arg Glu Glu Glu Asp Leu Ala Asn Cys Leu Val Met
145                 150                 155                 160

Leu Ser Asn Lys Ser Tyr Val Leu Ser Asp Asn Asn Glu Ala Thr Tyr
                165                 170                 175

Lys Ala Glu Glu Val Glu Lys Gly Met Phe Gln Cys Lys Ala Cys Lys
            180                 185                 190

Lys Val Phe Ser Ser His Gln Ala Leu Gly Gly His Arg Ala Ser His
        195                 200                 205

Lys Lys Val Lys Gly Cys Tyr Ala Ala Lys Ile Lys Asp Asp Asn Asp
    210                 215                 220

Gly Asn Asp Asn Asn Asp Asn Asn Asn Asp Asn Asp Ile Asp
225                 230                 235                 240

Glu Asp Ser Ile Ser Pro Ser Asp Leu Ile Phe His Gln Glu Ser Asn
                245                 250                 255

Ser Phe Gln Ser Gln Ser Pro Ser Ser Ser Ser Phe Ser Arg Lys
            260                 265                 270

Arg Ser Arg Val His Gln Cys Ser Ile Cys His Arg Val Phe Ser Ser
        275                 280                 285
```

```
Gly Gln Ala Leu Gly Gly His Lys Arg Cys His Trp Leu Ser Ser Ser
    290                 295                 300

Leu Pro Glu Asn Thr Phe Ile Pro Thr Phe Gln Ile Gln Tyr His
305                 310                 315                 320

Thr Gln Glu Gln Gly Leu Phe Asn Lys Pro Met Phe Thr Asn Phe Asp
                325                 330                 335

Gln Pro Leu Asp Leu Asn Phe Pro Ala Gln Leu Gly Asn Pro Ala Glu
                340                 345                 350

Phe Glu Leu Lys Leu His Asn Pro Phe Glu His Glu Gly Pro Arg Ser
            355                 360                 365

Tyr Leu Gln Leu Trp Thr Asp Gln Gln Ile Asn Thr Asn Leu His Gln
    370                 375                 380

Asn Glu Lys Cys Lys Asp Ser Thr Glu Asp Leu Arg Arg Glu Glu Asn
385                 390                 395                 400

Tyr Lys Asp Lys Glu Ala Lys Leu Ser Asn Leu Lys Asp Val Asn Leu
                405                 410                 415

Asp Gly Gly Ser Ser Trp Leu Gln Val Gly Ile Gly Pro Thr Pro Asp
                420                 425                 430

Ile Val Ala Thr Leu
            435

<210> SEQ ID NO 5
<211> LENGTH: 1948
<212> TYPE: DNA
<213> ORGANISM: Petunia hybrida
<220> FEATURE:
<221> NAME/KEY: CDS
<222> LOCATION: (130)..(1554)

<400> SEQUENCE: 5
cccccatgca attttttttag tctcttcatt ctctcaacta aaactagatt tgcttcttat      60
agtttcttgt ccatgtctct tctcattcat acttgaagta gtacaataac aagaaaataa     120 catttagcc atg gat tgt ata gat caa gaa caa caa caa caa caa cca gtt     171
          Met Asp Cys Ile Asp Gln Glu Gln Gln Gln Gln Gln Pro Val
            1               5                  10 ttt aag cat tat tgt aga gtt tgc aag aaa ggt ttt gtg tgt ggg aga       219
Phe Lys His Tyr Cys Arg Val Cys Lys Lys Gly Phe Val Cys Gly Arg
 15                  20                  25                  30 gct cta ggt ggg cat atg aga gct cat gga att ggg gat gaa gtt gta       267
Ala Leu Gly Gly His Met Arg Ala His Gly Ile Gly Asp Glu Val Val
                 35                  40                  45 act atg gat gat gat gat caa gca agt gat tgg gaa gat aag ttt gga       315
Thr Met Asp Asp Asp Asp Gln Ala Ser Asp Trp Glu Asp Lys Phe Gly
             50                  55                  60 ggg agt gtt aag gaa ggt aat aaa agg atg tac caa tta aga aca aac       363
Gly Ser Val Lys Glu Gly Asn Lys Arg Met Tyr Gln Leu Arg Thr Asn
 65                  70                  75 cct aat agg caa aaa agc aat aga gtt tgt gag aat tgt ggg aaa gaa       411
Pro Asn Arg Gln Lys Ser Asn Arg Val Cys Glu Asn Cys Gly Lys Glu
             80                  85                  90 ttc tct tct tgg aaa tct ttt ctt gaa cat gga aaa tgt agc tca gaa       459
Phe Ser Ser Trp Lys Ser Phe Leu Glu His Gly Lys Cys Ser Ser Glu
 95                 100                 105                 110 gat gca gaa gag tct tta gta tcc tcg ccc ggt tca gag ggc gag gat       507
Asp Ala Glu Glu Ser Leu Val Ser Ser Pro Gly Ser Glu Gly Glu Asp
                115                 120                 125 tac att tat gat gga aga aaa gaa aaa gga tac gga tgg tct aaa aga       555
```

```
                                     -continued

Tyr Ile Tyr Asp Gly Arg Lys Glu Lys Gly Tyr Gly Trp Ser Lys Arg
            130                 135                 140 aag agg tca tta aga aca aaa gta gga ggc ctt agt act tca act tat       603
Lys Arg Ser Leu Arg Thr Lys Val Gly Gly Leu Ser Thr Ser Thr Tyr
145                 150                 155 caa tca agt gag gaa gaa gat ctt ctc ctt gca aaa tgc ctt ata gat       651
Gln Ser Ser Glu Glu Glu Asp Leu Leu Leu Ala Lys Cys Leu Ile Asp
        160                 165                 170 tta gcc aat gca agg gtt gat aca tca ttg gtt gag cca gaa gag tct       699
Leu Ala Asn Ala Arg Val Asp Thr Ser Leu Val Glu Pro Glu Glu Ser
175                 180                 185                 190 tgt gcc tca gcc agt agg gag gag gaa cgg gcg gca cgg aac tcg atg       747
Cys Ala Ser Ala Ser Arg Glu Glu Glu Arg Ala Ala Arg Asn Ser Met
                195                 200                 205 gcc tac ggc ttc acc cca tta gtg agt act cgt gta ccc ttt gac aac       795
Ala Tyr Gly Phe Thr Pro Leu Val Ser Thr Arg Val Pro Phe Asp Asn
        210                 215                 220 aag gct aaa ggg gcg tct agt aaa ggg ttg ttt gaa tgt aaa gct tgc       843
Lys Ala Lys Gly Ala Ser Ser Lys Gly Leu Phe Glu Cys Lys Ala Cys
                225                 230                 235 aag aaa gtc ttc aat tcc cac caa gcc cta ggt gga cat agg gca agt       891
Lys Lys Val Phe Asn Ser His Gln Ala Leu Gly Gly His Arg Ala Ser
240                 245                 250 cac aag aaa gtt aag ggg tgt tat gca gcg aag caa gat caa ctc gat       939
His Lys Lys Val Lys Gly Cys Tyr Ala Ala Lys Gln Asp Gln Leu Asp
255                 260                 265                 270 gat atc tta att gat gat caa gat gtg aat atc aca cat gat caa gaa       987
Asp Ile Leu Ile Asp Asp Gln Asp Val Asn Ile Thr His Asp Gln Glu
                275                 280                 285 ttc ctg caa agt tca aaa tcc atg agg aag tca aaa atc cat gaa tgc       1035
Phe Leu Gln Ser Ser Lys Ser Met Arg Lys Ser Lys Ile His Glu Cys
                290                 295                 300 tca ata tgc cat aga gtt ttc tcg aca gga caa gct tta ggt ggt cac       1083
Ser Ile Cys His Arg Val Phe Ser Thr Gly Gln Ala Leu Gly Gly His
                305                 310                 315 aag agg tgc cac tgg atc acc tcc aat tcc ccc gat tct tcg aaa ttt       1131
Lys Arg Cys His Trp Ile Thr Ser Asn Ser Pro Asp Ser Ser Lys Phe
320                 325                 330 cat ttc aat ggt cat gtg gag caa att aat cta aga tca aac atg cat       1179
His Phe Asn Gly His Val Glu Gln Ile Asn Leu Arg Ser Asn Met His
335                 340                 345                 350 aaa tca gat gca tta gat ctt aat aac ctt ccg aca cat gaa gac atg       1227
Lys Ser Asp Ala Leu Asp Leu Asn Asn Leu Pro Thr His Glu Asp Met
                355                 360                 365 tcg cga att aga cga gac ccc ttt aat cca tta agc ttc gag gtg tca       1275
Ser Arg Ile Arg Arg Asp Pro Phe Asn Pro Leu Ser Phe Glu Val Ser
                370                 375                 380 aca gat ata cac ttg caa tat cca tgg agt tgt gct cca aaa aat gat       1323
Thr Asp Ile His Leu Gln Tyr Pro Trp Ser Cys Ala Pro Lys Asn Asp
                385                 390                 395 gat aat gac aat tac tac ctt gaa gaa att aaa atc gat agt aat gcc       1371
Asp Asn Asp Asn Tyr Tyr Leu Glu Glu Ile Lys Ile Asp Ser Asn Ala
        400                 405                 410 aac aac ggt aag tac aat att aat aat ggt gca aca caa aat gta gaa       1419
Asn Asn Gly Lys Tyr Asn Ile Asn Asn Gly Ala Thr Gln Asn Val Glu
415                 420                 425                 430 gat gat gaa gca gat agt aaa ttg aag tta gct aag cta agt gac cta       1467
Asp Asp Glu Ala Asp Ser Lys Leu Lys Leu Ala Lys Leu Ser Asp Leu
                435                 440                 445
```

-continued

```
aag gat atg aat acc aac tct gat aat ccc gcc cat tgg tta caa gtt        1515
Lys Asp Met Asn Thr Asn Ser Asp Asn Pro Ala His Trp Leu Gln Val
            450                 455                 460 ggg att ggt tca act aca gaa gta ggg gct gat tca taa gtaactatat         1564
Gly Ile Gly Ser Thr Thr Glu Val Gly Ala Asp Ser
        465                 470 gcagttattc ctttgcttaa tttcttttt ttctgtcacc cgagtatata tttatatgca      1624
aatattgtaa ttataacttc accaaacaga tagtaactgt ttggtgatgc aaatactgtt      1684
aatatttgta ctcccttttt ttttgtcctt ttcttgtaat tgatacacaa tcttgtaatt      1744
ttttgtactt tcaatttctt gagctgtaat tttcagtgta atacagaact cagaatatgt      1804
tattcttgca atatgaagtt tagtatgcaa cagtcaaaca cgattagtag aagtggtctg      1864
taatccctcc cactagttac aagttgggat tgattcaccc acagtagttg gggctgactt      1924
tgaagtaaac atatgcagtt attc                                             1948
```

<210> SEQ ID NO 6
<211> LENGTH: 474
<212> TYPE: PRT
<213> ORGANISM: Petunia hybrida

<400> SEQUENCE: 6

```
Met Asp Cys Ile Asp Gln Glu Gln Gln Gln Gln Pro Val Phe Lys
 1               5                  10                  15

His Tyr Cys Arg Val Cys Lys Lys Gly Phe Val Cys Gly Arg Ala Leu
            20                  25                  30

Gly Gly His Met Arg Ala His Gly Ile Gly Asp Glu Val Val Thr Met
        35                  40                  45

Asp Asp Asp Asp Gln Ala Ser Asp Trp Glu Asp Lys Phe Gly Gly Ser
    50                  55                  60

Val Lys Glu Gly Asn Lys Arg Met Tyr Gln Leu Arg Thr Asn Pro Asn
65                  70                  75                  80

Arg Gln Lys Ser Asn Arg Val Cys Glu Asn Cys Gly Lys Glu Phe Ser
                85                  90                  95

Ser Trp Lys Ser Phe Leu Glu His Gly Lys Cys Ser Ser Glu Asp Ala
            100                 105                 110

Glu Glu Ser Leu Val Ser Ser Pro Gly Ser Glu Gly Glu Asp Tyr Ile
        115                 120                 125

Tyr Asp Gly Arg Lys Glu Lys Gly Tyr Gly Trp Ser Lys Arg Lys Arg
    130                 135                 140

Ser Leu Arg Thr Lys Val Gly Gly Leu Ser Thr Ser Thr Tyr Gln Ser
145                 150                 155                 160

Ser Glu Glu Glu Asp Leu Leu Leu Ala Lys Cys Leu Ile Asp Leu Ala
                165                 170                 175

Asn Ala Arg Val Asp Thr Ser Leu Val Glu Pro Glu Ser Cys Ala
            180                 185                 190

Ser Ala Ser Arg Glu Glu Glu Arg Ala Ala Arg Asn Ser Met Ala Tyr
        195                 200                 205

Gly Phe Thr Pro Leu Val Ser Thr Arg Val Pro Phe Asp Asn Lys Ala
    210                 215                 220

Lys Gly Ala Ser Ser Lys Gly Leu Phe Glu Cys Lys Ala Cys Lys Lys
225                 230                 235                 240

Val Phe Asn Ser His Gln Ala Leu Gly Gly His Arg Ala Ser His Lys
                245                 250                 255

Lys Val Lys Gly Cys Tyr Ala Ala Lys Gln Asp Gln Leu Asp Asp Ile
```

-continued

```
                    260                 265                 270
Leu Ile Asp Asp Gln Asp Val Asn Ile Thr His Asp Gln Glu Phe Leu
            275                 280                 285
Gln Ser Ser Lys Ser Met Arg Lys Ser Lys Ile His Glu Cys Ser Ile
        290                 295                 300
Cys His Arg Val Phe Ser Thr Gly Gln Ala Leu Gly Gly His Lys Arg
305                 310                 315                 320
Cys His Trp Ile Thr Ser Asn Ser Pro Asp Ser Ser Lys Phe His Phe
                    325                 330                 335
Asn Gly His Val Glu Gln Ile Asn Leu Arg Ser Asn Met His Lys Ser
                340                 345                 350
Asp Ala Leu Asp Leu Asn Asn Leu Pro Thr His Glu Asp Met Ser Arg
            355                 360                 365
Ile Arg Arg Asp Pro Phe Asn Pro Leu Ser Phe Glu Val Ser Thr Asp
        370                 375                 380
Ile His Leu Gln Tyr Pro Trp Ser Cys Ala Pro Lys Asn Asp Asp Asn
385                 390                 395                 400
Asp Asn Tyr Tyr Leu Glu Glu Ile Lys Ile Asp Ser Asn Ala Asn Asn
                    405                 410                 415
Gly Lys Tyr Asn Ile Asn Asn Gly Ala Thr Gln Asn Val Glu Asp Asp
                420                 425                 430
Glu Ala Asp Ser Lys Leu Lys Leu Ala Lys Leu Ser Asp Leu Lys Asp
            435                 440                 445
Met Asn Thr Asn Ser Asp Asn Pro Ala His Trp Leu Gln Val Gly Ile
        450                 455                 460
Gly Ser Thr Thr Glu Val Gly Ala Asp Ser
465                 470
```

<210> SEQ ID NO 7
<211> LENGTH: 2712
<212> TYPE: DNA
<213> ORGANISM: Petunia hybrida
<220> FEATURE:
<221> NAME/KEY: misc_feature
<222> LOCATION: (1)..(2624)
<223> OTHER INFORMATION: promoter
<220> FEATURE:
<221> NAME/KEY: misc_feature
<222> LOCATION: (1)...(2712)
<223> OTHER INFORMATION: n = A,T,C or G

<400> SEQUENCE: 7

```
ctgcaggcag caacattagg agattttcca gcaccaatct ccctatgtgc tataacttca      60
cttataggca tggtattgac tggaattgta caattgatac aacaagggtc gttggagatt     120
ggattgcccc tgttaagcat ccgtgactta ataggctact cgttattggt aattcatcaa     180
atatccctga aattctcaca ttaattatgt taatacagaa attctgagtt agatttgact     240
tacatacgtt gatagcctaa ataatttgta tgatactaac gttttttttaa cctgatactt     300
tatattaact ttgaggtttg tctaattttt tgtggttatc ataggcaggt atagttagtg     360
gagcatgtgt aagtttcaat aattgggcaa tgaagaaaag agggccagtc ttagtttccg     420
tatttagtcc tgttggaact gtgataactg tcgtactttc tgctatcacc ttgaagtaca     480
caattactat gggaaggtaa aaccttatcc attttcactt ggatctagct tatatacagt     540
gtaaagaaat ttttacaata ttttccaagt aacttttaaa gacgattatc ataatcatg     600
ttttacttaa cctgatagtg taaatatatt ttttcacact tacaattact ttagttcttt     660
```

```
ttcagttgca tcaaaattca aacttcaaat gacttaactt cttttttgcag ccttggtggt      720 atgtttctca tgtttacggg tctgtatttc gtgttatggg ctaaaaggaa cgaaggattt      780
ctaaataata ccaactcctc agaaagtgag tacgatgttg agaagcctct tttgcattaa      840
atttcttttt attctcaatt gtaatatgta gttagtttgt atatacaact agaatccaac      900
atagagaaga gagagggaga gcttgtttgt accaaataga taacatgtat gttgatttaa      960
gtatcccata ttggtactgg aagtanactg ttaatgttgc ctgcgattca attgtccagt     1020
ccttggtgta gtgagacagt gttaaatatc ccacatggta taaaaaatgg attgctgtct     1080
ccttatatgg tatttgacaa tcctcacatt ttgagctaaa atttggggttg agttaatgca     1140 attgtccatt tcttatcaat gtatttaatc taggcttgga gctaaaaata caaagcaaaa     1200
gagaagagag aaaaagaaca agaaagact attatgatga ttgatatttg aaaaaatgca     1260
agttccaatc ctagtaatat cttttatttt gcagtagcat gacggaatat gggaatcaac     1320
atgtagctgc ttttctggct ctatctaagc ccctcttctt ttaccatagt tttgttttttc     1380 attcactttt ggaagcagca agggtagatt tagaccacaa atatgcaaat gtttttttt     1440 tttttttttt tgtaaagtct tagacctata tggagtataa cctttgggaa agggggttga     1500
atcaatgatc ataatgtcac aatcatgtag tactacattt tttgttcttc aatttgagct     1560
actagtttga catttcccaa gtaaattatg cttcaacact aggattctct tgtttatatt     1620
atctcattga agctatgctt taactctctt ccttgagtgg attaacttga aaaagtaggc     1680
aaagaaattt atgagagttc tgatatcgat atcatagagg acacaaaatt aagaaaatgc     1740
gaaaagactt atacccaaca aagaaaatat gaacactagt atcgatcacc acccagattt     1800
acaatttaat gtactggtgt tcaattttgt gcttgcatcg actatttcac cgaatattta     1860
ttcttattta taaaaatatc gaataactat gaccatcaaa gtttagccaa ataaaatata     1920
aaaaagtatc tatatcacta tagtaaactt tgtatttatt ggaattgaac tcacacttct     1980
tccattacta ggtcaaatcc cagaaggcat attataagtt tttgtttcaa agcctccaaa     2040
ccaagtacac tcattttctt tttgaagaaa gcgagttcat ttgtaggcta cgtgaatata     2100
actactttaa aatattgctt tgtttcgaat ttgccatgag ttactacatt cacacaaaat     2160
tcttaatgcg actcagagtg tgtgttttaa ttttctttta gagtgtttgt acttctatat     2220
gagggtcact agtaaagtag tccactaata ttacaaattc ttacattacg tacaatgtga     2280
ttttatgtca gtagatttga ctgaatgcta taactacgag agttagaaat agtctttgcc     2340
aaccacatta taaactgacc ctccacttgt cataacaaac tctcttgttc tcatccacaa     2400
ctaactttaa ctagaaacta ggacttccct cacttatgct acaaaaatcc ttataactac     2460
accacaacct ttagtactgt tcactaacta attctttatt tataccaacc ctggcttgga     2520
gtgtagcaaa aaaatgtaca ctactccaaa gtaaacacta ttctttgaaa ctttccttgt     2580
tgcactttaa tttatgttct agtgagtata ttagagagtg agaaatggtg gacaatagcc     2640
agaaaaatga accatcaact gttatacact attgtagagt atgtaaaagg ggatttaata     2700
ngtntggagc tc                                                         2712
```

<210> SEQ ID NO 8
<211> LENGTH: 4002
<212> TYPE: DNA
<213> ORGANISM: Petunia hybrida
<220> FEATURE:
<221> NAME/KEY: misc_feature
<222> LOCATION: (1)..(3631)
<223> OTHER INFORMATION: promoter
<220> FEATURE:
<221> NAME/KEY: misc_feature
<222> LOCATION: (1)...(4002)
<223> OTHER INFORMATION: n = A,T,C or G

<400> SEQUENCE: 8

```
gaattcacca ccacgagtac ttattttgat gagcatggca ttattttca aacttcttgt      60
gctggaacac cacagcagaa cgggaaagtt gagcgaaaac ataaacatat tttgaatgtt     120
gctcgagcac ttaggtttca agcgcatttc ccaattgagt tttggggtga gtgtgttttg     180
atggcgtgct atttgatcaa gcgaaccctc tcatcggtct tacacagaaa aaaatgccat     240
atgatgtctt ttttggtgta acaccgaact acgagcattt gaaagtgttt ggatctctat     300
gctatggtca caagcatggg tgcttgggag ataagtttga agtaggagt cgtctgtgtg     360
ttttattgg atacccatat gggaagaaat catggaagtt atatgatttg dacaccaaaa     420
aatattttgt gtcgcgggca cctagcaccg aagcactaag catccgaacc caacgttatt     480
tcagcctatg agagtgattg aagatgacta tggtattgaa gtgagggggt agtgacactg     540
ttttgacaca aaaaccgaac aaggagagga tacagctcga ggacgtgata attgacactc     600
caagtttggc tacagagact aatgtcatgg aagtagaaaa cccggtcacc ggtgtcatgt     660
ccgatcaatt gaangctgaa gctgtgggag aagagttggg tcgagaaaac taattaggaa     720
ggagaatgtc tccttcgtga ttttcactg gtctgtcgaa aggttagtca ccaggtttca     780
acctgtgtcc acatgtctga tttctcaccc gtgacacaac gagcctcagg tacgccttat     840
cctcttacac actatgttaa ttgtgaccgt ttttcttcga agcatgtgag ttttcttgca     900
gctattacgg agggtcgtga atcgacctct ttctgtgtgg ccataaagaa tgaaaaatgg     960
agaaagacta tgcaatagga gtttcaagca ttggaagata ataaacatc tatggttggt    1020
tacttgccac ctgggaagaa agcgctcgga tgtcggtggg tgtataagat caaatataat    1080
tccgatggat cagtggtacg atacaaggca cgtttggtta gttttggaaa tcatcaggtc    1140
aaaggcattg attatacgta gacatttgct ccagtcgcta aaatagtgac tttgaggaca    1200
tttcttgcag tcgctgcagc taaaaattgg gaattgcatc aaatggatgt tcataatgca    1260
tttgtacagg tgatcttcat gaaaaagtct atatgaagct gccaccaagg tatcagacta    1320
atggttacgg taatgtgtgt cgcctatgaa agttttgta tggtttgaag caggcgtcga    1380
gatgttggtt cacgaagtta ttggccgatt tgaaaactta tgcttttana caatcttatt    1440
cggattatg ccttttaca cttcgtaaag ggtccgtcac cttaagtgtg ttggtgtacg    1500
tggatgattt gattattggg gcaataattc ggaagctatt cgtctcttta agttgtatct    1560
ctccacttgc tttcttatga agatttggg catactaaat tttttgggag atgaagtggc    1620
tagaggacct aaaggtattt tcctatgtca atggaaatat gccttggata taattggatt    1680
attaggagct cgactggttg gaacttctat ggagcagaat catcgtttgg ctttggcaag    1740
tggccgatat attgatgatc tacatagata tatttgattg atgattctag tgcttaatta    1800
aagactgatc aattgtactg ttattaatta atctttgttt aggaggagca tgtgggctgg    1860
aaaatgatgt agcaaacttt ccatacaatg ccatgattac tgcaggaaat gaagtcctat    1920
ttaaacatgg ctttggctgt ggtgcatgct accaggtgca cttgaaattt gttttataaa    1980
aagagaaaca catgcatgaa ttttgagttt cacttcgcaa aataaatgaa atctttattt    2040
atattaatgc aatcgatttt caggtgttgt gcttacagaa tcaaaatcaa tactgctcag    2100
gaaatccaat aatagtaact nttacagatg agtgcccagg ggcatgcaat aatgatcctg    2160
```

```
ttcattttga ttttagtgga actgcttttg gagccttggc aaaacctggc caagctgaac    2220
aattgcgtaa tgaaggaaga atccaaatta attacagaag gtgagttacg ttccacatga    2280
caaatagaga aatcaataca aaatttccat ttacttagta acactctttc cttgttagta    2340
tgcctaaaaa agagtagtac acaacacaat taatgcacaa ttttgctaaa ccatgatatt    2400
gaatcgtgca gagtggcatg cagttacaag gcaaatatac aatttaaggt agacaaaggc    2460
tccaatcctg atttcttggc agttgcagct gaggcagtta atggagatgg tgatctttct    2520
tttgtagaaa ttaaagcatc caattcgaat caatggcttc ccatgcaaca aatgtttggg    2580
gcaacttgga gcgttggcat caagccagac acacagaaac ctcctttctc acttagactt    2640
actacagaat ttaagcaaac agtcattgcc caaatgtca taccagtggg ttggcaacca    2700
agagcaattt acaaatcaaa tgtcaatttc ccacccaagc tttagtttaa tcttttttacc   2760 cacaatagtg taaaaataat tataaggact acaaattaaa tactctatgt tcaacagtgc    2820
tatttaatta taataaggat tacaaattaa agtgaggatt cttctcaatg ataatgtcaa    2880
aagtttggga tgtcaaatct atttgtattt tttttcacat caatgatcaa tgaaagttat    2940
gcttttagta ttttttaatt attaataatt tgttttcatg tatttcaata ataatattat    3000
ctcaaaagta aataaatcaa tattcaaaac tgacatgaaa attttcattc tcactatatt    3060
tatgttcttt tttcagtctc aaacgcccaa attttgtacg aaaaaattgt tcggataagc    3120
gagaaacact cataactgat aaaaacagaa tagtgaataa agaaaactaa atatatttac    3180
tcttgatgag tccatgatgt gtaagtatta tcttctgccg tccaatttgg ttgtttgaca    3240
ccactagtgt tattaataaa aagtttgtga aaaaataagc tcttcactcc cttaggcctt    3300
actctctcct tccacttgtc atactcactc ttcacttcca ctcacactcc tatttttctc    3360
tttacctcta aactctcctc cacaaaccac tacttcaact aaaaactagg actaattttt    3420
ttctcaccgt acaagtccac aacaacttct agtacaagaa caaacaaact ctcgttgtgc    3480
ccctcgctcc catgcatgca caccccccatg caattttttt agtctcttca ttctctcaac    3540
taaaactaga tttgcttctt atagtttctt gtccatgtct cttctcattc atacttgaag    3600
tagtacaata acaagaaaat aacatttagc catggattgt atagatcaag aacaacaaca    3660
acaacaacca gttttaagc attattgtag agtttgcaag aaaggttttg tgtgtgggag    3720
agctctaggt gggcatatga gagctcatgg aattggggat gaagttgtaa ctatggatga    3780
tgatgatcaa gcaagtgatt gggaagataa gtttggaggg agtgttaagg aaggtaataa    3840
aaggatgtac caattaagaa caaaccctaa taggcaaaaa agcaatagag tttgtgagaa    3900
ttgtgggaaa gaattcctgc agcccggggg atccactagt tctagagcng ngcgcaccgc    3960
ggtggagctc cagcttttgt tcccttttacg tgagggttaa tt                     4002
```

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (6)
<223> OTHER INFORMATION: n = inosine
<220> FEATURE:
<221> NAME/KEY: modified_base
<222> LOCATION: (9)
<223> OTHER INFORMATION: n = inosine
<220> FEATURE:
<221> NAME/KEY: modified_base

```
<222> LOCATION: (12)
<223> OTHER INFORMATION: n = inosine
<220> FEATURE:
<221> NAME/KEY: modified_base
<222> LOCATION: (15)
<223> OTHER INFORMATION: n = inosine

<400> SEQUENCE: 9
cargcnytng gnggncay                                              18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (6)
<223> OTHER INFORMATION: n = inosine
<220> FEATURE:
<221> NAME/KEY: modified_base
<222> LOCATION: (9)
<223> OTHER INFORMATION: n = inosine
<220> FEATURE:
<221> NAME/KEY: modified_base
<222> LOCATION: (12)
<223> OTHER INFORMATION: n = inosine
<220> FEATURE:
<221> NAME/KEY: modified_base
<222> LOCATION: (15)
<223> OTHER INFORMATION: n = inosine

<400> SEQUENCE: 10
gtycgnranc cnccngtr                                              18

<210> SEQ ID NO 11
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 11
ctgttatcgg tcttttttact tggtagttga cagctgctcg aggtat              46

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 12
ctatatccta ggataggt ac                                           22

<210> SEQ ID NO 13
<211> LENGTH: 1886
<212> TYPE: DNA
<213> ORGANISM: Petunia hybrida
<220> FEATURE:
<221> NAME/KEY: CDS
<222> LOCATION: (283)..(1617)

<400> SEQUENCE: 13
cccacgcgtc cgcatgtgca gagataaata taaaccaaca tgacctacca ttaagatgag      60
acgatgatca tctaaaattt tggagctcag atgattttat tcgacaaatt tcctatttc     120 tcgctatggg tttccttttc agctaagcta cctccctcct tcttcttgat ttgattttct    180
```

```
tgggtttctt gtttcttctt gttttagggt ttttgataca catatatagt tgcttagtta      240
cgtagctaag taaggtgggt tatttcattt cttgaacttt ca atg gtt gat tat         294
                                             Met Val Asp Tyr
                                              1 caa gat ctt caa gtt ggg atg agc gga aca ctg tgg ata caa ctc aag        342
Gln Asp Leu Gln Val Gly Met Ser Gly Thr Leu Trp Ile Gln Leu Lys
 5              10                  15                  20 att gaa gac aaa caa gtt caa gaa ttg gat cat agt caa gat att atg        390
Ile Glu Asp Lys Gln Val Gln Glu Leu Asp His Ser Gln Asp Ile Met
            25                  30                  35 gac tat gag gtt cca aaa aat aat gat cat act agg att tgt gag gtg        438
Asp Tyr Glu Val Pro Lys Asn Asn Asp His Thr Arg Ile Cys Glu Val
                40                  45                  50 tgt aac aaa ggg ttt agc tca ggt aaa gca ctt ggg ggt cac atg aga        486
Cys Asn Lys Gly Phe Ser Ser Gly Lys Ala Leu Gly Gly His Met Arg
        55                  60                  65 att cac gtt cag gct gcc aaa aag ctc tta tct gtt ggt aaa aag tgc        534
Ile His Val Gln Ala Ala Lys Lys Leu Leu Ser Val Gly Lys Lys Cys
    70                  75                  80 aaa aag ctg aac cca ttc ggt tcc agg tat tac aag aaa cga ata tta        582
Lys Lys Leu Asn Pro Phe Gly Ser Arg Tyr Tyr Lys Lys Arg Ile Leu
85                  90                  95                  100 tta caa caa gat gat cat caa gat aat tac aac aat gac atc aag aat        630
Leu Gln Gln Asp Asp His Gln Asp Asn Tyr Asn Asn Asp Ile Lys Asn
                105                 110                 115 cag ttg gca cca att tgt tca gtt tgt ggt aag aat ttt cca tca atg        678
Gln Leu Ala Pro Ile Cys Ser Val Cys Gly Lys Asn Phe Pro Ser Met
            120                 125                 130 aaa tca ttg ttt ggg cat atg aga tct cat cct gaa agg gcc tgg aga        726
Lys Ser Leu Phe Gly His Met Arg Ser His Pro Glu Arg Ala Trp Arg
        135                 140                 145 gga att caa cct cca gct cct aat aaa aac agt tgt ttg tca tca gct        774
Gly Ile Gln Pro Pro Ala Pro Asn Lys Asn Ser Cys Leu Ser Ser Ala
    150                 155                 160 tcc aat gaa att gct gct act act aag tcg ggg gat tta tcg gtg cct        822
Ser Asn Glu Ile Ala Ala Thr Thr Lys Ser Gly Asp Leu Ser Val Pro
165                 170                 175                 180 ggt tgg tct gtt aag gct aag cga ggc cga aag ggt act att gct gaa        870
Gly Trp Ser Val Lys Ala Lys Arg Gly Arg Lys Gly Thr Ile Ala Glu
                185                 190                 195 gca tca tct aac tcg agt ctt ggt tct aga agt ttc tct ttt gat caa        918
Ala Ser Ser Asn Ser Ser Leu Gly Ser Arg Ser Phe Ser Phe Asp Gln
            200                 205                 210 gaa aag gat gac gag gag cac gaa tta cac gat gct gtt ggt cat ctt        966
Glu Lys Asp Asp Glu Glu His Glu Leu His Asp Ala Val Gly His Leu
        215                 220                 225 atg ttg tta gcc aat gga aat aag act agt gca gat caa gaa ttg gaa       1014
Met Leu Leu Ala Asn Gly Asn Lys Thr Ser Ala Asp Gln Glu Leu Glu
    230                 235                 240 ata acc aac agt aat tcg ctt act tcc aaa gct gaa act gaa caa gtc       1062
Ile Thr Asn Ser Asn Ser Leu Thr Ser Lys Ala Glu Thr Glu Gln Val
245                 250                 255                 260 gat gag aac aag aag aaa aag aag aag ata aag tta agg cgt ttg ggt       1110
Asp Glu Asn Lys Lys Lys Lys Lys Lys Ile Lys Leu Arg Arg Leu Gly
                265                 270                 275 tct gta caa gac ctt gtt agt cca gtt tca gtt cat cat gac caa aaa       1158
Ser Val Gln Asp Leu Val Ser Pro Val Ser Val His His Asp Gln Lys
            280                 285                 290
```

```
cta gtc atg gat acg cct gaa aaa tac aaa tgt aac act tgt gaa aag      1206
Leu Val Met Asp Thr Pro Glu Lys Tyr Lys Cys Asn Thr Cys Glu Lys
            295                 300                 305 agc ttt gca act cat caa gca ctg gga gga cat agg tca agc cac aac      1254
Ser Phe Ala Thr His Gln Ala Leu Gly Gly His Arg Ser Ser His Asn
310                 315                 320 aag ttt aga atg gtc att caa aat tca gtt gaa gat gat gta gtt act      1302
Lys Phe Arg Met Val Ile Gln Asn Ser Val Glu Asp Asp Val Val Thr
325                 330                 335                 340 aat gta gca act agt agc ata att ggc cca gtg gaa gaa cgt gaa gaa      1350
Asn Val Ala Thr Ser Ser Ile Ile Gly Pro Val Glu Glu Arg Glu Glu
                345                 350                 355 gca gct gct agc acc tca aaa ttg ttg gtg gac cat aac aag aat gcc      1398
Ala Ala Ala Ser Thr Ser Lys Leu Leu Val Asp His Asn Lys Asn Ala
            360                 365                 370 tca gca agt cag gta ctt ggg gtt cag aat agg tgc caa tgg gga agt      1446
Ser Ala Ser Gln Val Leu Gly Val Gln Asn Arg Cys Gln Trp Gly Ser
        375                 380                 385 cca att gat cat caa gct ggt cca tca aca agt caa ttg act tca cca      1494
Pro Ile Asp His Gln Ala Gly Pro Ser Thr Ser Gln Leu Thr Ser Pro
390                 395                 400 ggt gaa gtt agc cat tca att ggt cga caa att ctg gat ttt gat ctc      1542
Gly Glu Val Ser His Ser Ile Gly Arg Gln Ile Leu Asp Phe Asp Leu
405                 410                 415                 420 aat gaa tta ccc cct caa gaa gat gaa att gct ggt ggc cgt gat cat      1590
Asn Glu Leu Pro Pro Gln Glu Asp Glu Ile Ala Gly Gly Arg Asp His
                425                 430                 435 cag tat ttt aca ttt ttt cca att taa ctactcctag gtagtgtttg           1637
Gln Tyr Phe Thr Phe Phe Pro Ile
            440 tttagtctac agcttttaac tcttagctgg ttaggaatta acagctacta cttcatcatc    1697 agtgagaaag gccagtcatg taagttttgg catgttaatg atccatttac tagtagtgca    1757 aattgtggat aatagcgaac catcttggtt atttccattt ttttgctagt tttccataac    1817 aatgtggcat tttgaagaaa gggctgttga actttttttt cttatatctt catggaaagt    1877 acgatgttt                                                            1886

<210> SEQ ID NO 14
<211> LENGTH: 444
<212> TYPE: PRT
<213> ORGANISM: Petunia hybrida

<400> SEQUENCE: 14

Met Val Asp Tyr Gln Asp Leu Gln Val Gly Met Ser Gly Thr Leu Trp
1               5                   10                  15

Ile Gln Leu Lys Ile Glu Asp Lys Gln Val Gln Glu Leu Asp His Ser
            20                  25                  30

Gln Asp Ile Met Asp Tyr Glu Val Pro Lys Asn Asn Asp His Thr Arg
        35                  40                  45

Ile Cys Glu Val Cys Asn Lys Gly Phe Ser Ser Gly Lys Ala Leu Gly
    50                  55                  60

Gly His Met Arg Ile His Val Gln Ala Ala Lys Lys Leu Leu Ser Val
65                  70                  75                  80

Gly Lys Lys Cys Lys Lys Leu Asn Pro Phe Gly Ser Arg Tyr Tyr Lys
                85                  90                  95

Lys Arg Ile Leu Leu Gln Gln Asp Asp His Gln Asp Asn Tyr Asn Asn
            100                 105                 110
```

```
Asp Ile Lys Asn Gln Leu Ala Pro Ile Cys Ser Val Cys Gly Lys Asn
            115                 120                 125

Phe Pro Ser Met Lys Ser Leu Phe Gly His Met Arg Ser His Pro Glu
        130                 135                 140

Arg Ala Trp Arg Gly Ile Gln Pro Pro Ala Pro Asn Lys Asn Ser Cys
145                 150                 155                 160

Leu Ser Ser Ala Ser Asn Glu Ile Ala Ala Thr Thr Lys Ser Gly Asp
                165                 170                 175

Leu Ser Val Pro Gly Trp Ser Val Lys Ala Lys Arg Gly Arg Lys Gly
            180                 185                 190

Thr Ile Ala Glu Ala Ser Ser Asn Ser Ser Leu Gly Ser Arg Ser Phe
        195                 200                 205

Ser Phe Asp Gln Glu Lys Asp Glu Glu His Glu Leu His Asp Ala
        210                 215                 220

Val Gly His Leu Met Leu Leu Ala Asn Gly Asn Lys Thr Ser Ala Asp
225                 230                 235                 240

Gln Glu Leu Glu Ile Thr Asn Ser Asn Ser Leu Thr Ser Lys Ala Glu
                245                 250                 255

Thr Glu Gln Val Asp Glu Asn Lys Lys Lys Lys Lys Ile Lys Leu
            260                 265                 270

Arg Arg Leu Gly Ser Val Gln Asp Leu Val Ser Pro Val Ser Val His
        275                 280                 285

His Asp Gln Lys Leu Val Met Asp Thr Pro Glu Lys Tyr Lys Cys Asn
        290                 295                 300

Thr Cys Glu Lys Ser Phe Ala Thr His Gln Ala Leu Gly Gly His Arg
305                 310                 315                 320

Ser Ser His Asn Lys Phe Arg Met Val Ile Gln Asn Ser Val Glu Asp
                325                 330                 335

Asp Val Val Thr Asn Val Ala Thr Ser Ser Ile Ile Gly Pro Val Glu
            340                 345                 350

Glu Arg Glu Glu Ala Ala Ala Ser Thr Ser Lys Leu Leu Val Asp His
        355                 360                 365

Asn Lys Asn Ala Ser Ala Ser Gln Val Leu Gly Val Gln Asn Arg Cys
        370                 375                 380

Gln Trp Gly Ser Pro Ile Asp His Gln Ala Gly Pro Ser Thr Ser Gln
385                 390                 395                 400

Leu Thr Ser Pro Gly Glu Val Ser His Ser Ile Gly Arg Gln Ile Leu
                405                 410                 415

Asp Phe Asp Leu Asn Glu Leu Pro Pro Gln Glu Asp Glu Ile Ala Gly
            420                 425                 430

Gly Arg Asp His Gln Tyr Phe Thr Phe Phe Pro Ile
        435                 440
```